United States Patent
Terán Moldes et al.

(10) Patent No.: US 10,253,000 B2
(45) Date of Patent: Apr. 9, 2019

(54) PYRIDAZIN-3(2H)-ONE DERIVATIVES AS MONOAMINE OXIDASE SELECTIVE ISOFORM B INHIBITORS

(71) Applicants: UNIVERSIDADE DE VIGO, Vigo (Pontevedra) (ES); UNIVERSIDADE DE SANTIAGO DE COMPOSTELA, Santiago de Compostela (La Coruña) (ES)

(72) Inventors: M$^a$ del Carmen Terán Moldes, Vigo (ES); Pedro Besada Pereira, Vigo (ES); Tamara Costas Caamaño, Vigo (ES); M$^a$ del Carmen Costas Lago, Vigo (ES); Noemí Vila Molares, Vigo (ES); Dolores Viña Castelao, Vigo (ES)

(73) Assignees: UNIVERSIDADE DE VIGO, Vigo (Pontevedra) (ES); UNIVERSIDADE DE SANTIAGO DE COMPOSTELA, Santiago de Compostela (la Coruña) (ES)

( * ) Notice: Subject to any disclaimer, the term of this patent is extended or adjusted under 35 U.S.C. 154(b) by 0 days.

(21) Appl. No.: 15/301,127

(22) PCT Filed: Mar. 3, 2015

(86) PCT No.: PCT/ES2015/000029
§ 371 (c)(1),
(2) Date: Sep. 30, 2016

(87) PCT Pub. No.: WO2015/132427
PCT Pub. Date: Sep. 11, 2015

(65) Prior Publication Data
US 2018/0215718 A1  Aug. 2, 2018

(30) Foreign Application Priority Data
Mar. 4, 2014 (ES) .................................. 201400162

(51) Int. Cl.
| | | |
|---|---|---|
| *C07D 237/14* | (2006.01) | |
| *A61P 25/28* | (2006.01) | |
| *A61K 31/50* | (2006.01) | |
| *A61K 31/501* | (2006.01) | |
| *A61K 31/5377* | (2006.01) | |
| *A61K 45/06* | (2006.01) | |

(52) U.S. Cl.
CPC ............ *C07D 237/14* (2013.01); *A61K 31/50* (2013.01); *A61K 31/501* (2013.01); *A61K 31/5377* (2013.01); *A61K 45/06* (2013.01); *A61P 25/28* (2018.01)

(58) Field of Classification Search
CPC ....... C07D 237/14; A61P 25/28; A61K 31/50; A61K 31/501; A61K 31/5377; A61K 45/06

See application file for complete search history.

(56) References Cited

FOREIGN PATENT DOCUMENTS

| EP | 1061077 A1 | 12/2000 |
|---|---|---|
| EP | 1130015 A1 | 9/2001 |
| WO | 8200402 A1 | 2/1982 |

OTHER PUBLICATIONS

International Search Report and Written Opinion for International Application No. PCT/ES2015/000029 (dated Apr. 30, 2015) (10 Pages).

*Primary Examiner* — Sahar Javanmard
(74) *Attorney, Agent, or Firm* — Lucas & Mercanti, LLP

(57) ABSTRACT

The present invention refers to pyridazin-3(2H)-one derivatives of general structure I, II and III, which are selective MAO-B inhibitors, and to the use thereof for preparing medicaments intended to treat disorders derived from MAO-B hyperactivity, particularly degenerative disorders of the central nervous system (CNS), such as Parkinson's disease (PD), Alzheimer's disease (AD) and other dementias. These are pyridazin-3(2H)-one derivatives having dithiocarbamate moieties bonded to position 4, 5 or 6 through an alkyl chain of variable length (n=1, 2, 3). This invention is also directed to the preparation of said compounds.

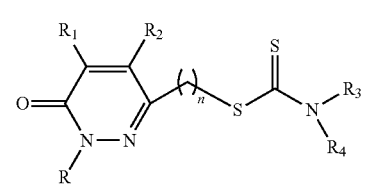

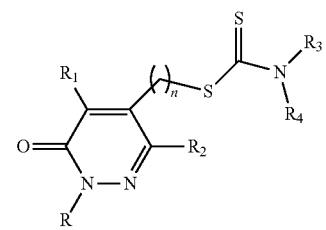

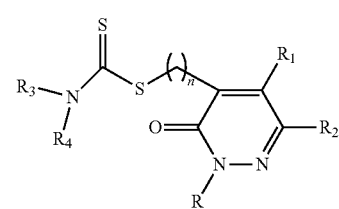

12 Claims, No Drawings

PYRIDAZIN-3(2H)-ONE DERIVATIVES AS MONOAMINE OXIDASE SELECTIVE ISOFORM B INHIBITORS

CROSS REFERENCE TO RELATED APPLICATION

This Application is a 371 of PCT/ES2015/000029 filed on Mar. 3, 2015, which claims the benefit of Spanish Patent Application No. P201400162 filed on March 2014, both of which are incorporated herein by reference.

TECHNICAL FIELD

The present invention refers to novel C4-, C5- or C6-substituted pyridazinone derivative compounds having a dithiocarbamate moiety, and of general structure I, II and III, respectively, which are selective MAO-B inhibitors, and to the use thereof for preparing medicaments intended to treat disorders derived from MAO-B hyperactivity, particularly degenerative disorders of the central nervous system (CNS), such as Parkinson's disease (PD), Alzheimer's disease (AD) and other dementias.

These are pyridazin-3(2H)-one having dithiocarbamate moieties bonded to position 4, 5 or 6 through an alkyl chain of variable length. The general structural formulae of the 3 series of compounds, structures I, II and III, are detailed below.

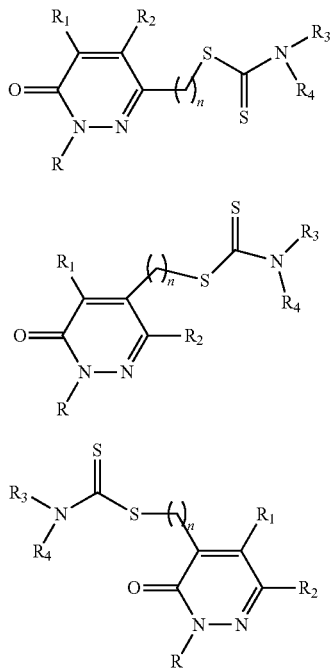

State of the Art

The monoamine oxidases (MAO) are flavoenzymes being present in the outer membrane of CNS cells and peripheral tissue mitochondria, wherein they catalyse the oxidative deamination of endogenous or exogenous amines so as to generate the corresponding aldehydes, ammonia and $H_2O_2$. Two MAO isoenzymes are known, designated as MAO-A and MAO-B, which share approximately 70% of the amino acid sequence and which are differentiated by the three dimensional structure thereof, by the substrate selectivity and by the existence of selective inhibitors (Proc. Natl. Acad. Sci. USA 105, 5739-5744, 2008; J. Biol. Chem. 280(16), 15761-15766, 2005). Both isoenzymes play an important role in the regulation of biogenic amines concentration in the brain; this fact, together with the substrate selectivity, determines the clinical importance of the MAO inhibitors (MAOIs). Thus, the MAO-A shows higher affinity for serotonin (5-hydroxytryptamine, 5-HT), adrenaline (A) and noradrenaline (NA), and it is selectively inhibited by clorgiline and moclobemide, whereas MAO-B preferably degrades 3-phenylethylamine and benzylamine and it is selectively inhibited by selegiline and rasagiline. There are some MAOIs which feature lack of selectivity, such as iproniazid.

The structure of the MAOI compounds cited above is detailed in figure 1.

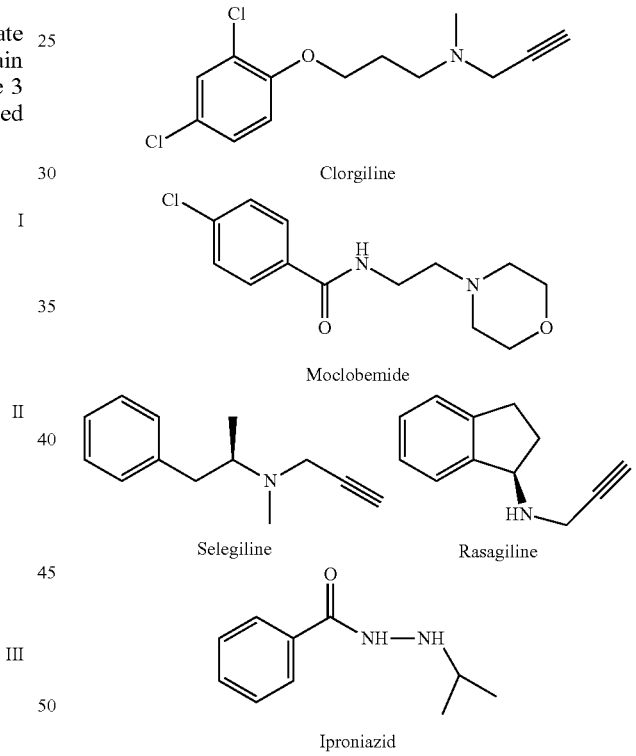

FIG. 1

Functional studies about both enzymes have revealed that MAOs play an important role in the regulation of biogenic amines concentration in the brain, which are involved in different pathological processes affecting the CNS, which determines the clinical importance of MAOIs (Curr. Med, Chem. 11, 2033-2043, 2004). MAO-A inhibition in the CNS enhances noradrenaline and serotonin levels, two neurotransmitters involved in depressive disorders, whereas MAO-B inhibition increase dopamine levels, which in PD are reduced, which explains that MAOI-A are used as antidepressants and anxiolytics, and MOIs-B for EP treatment.

The AD is a progressive neurodegenerative disease which is the most habitual type of senile dementia. Although the aetiology thereof is multiple and complex, it is associated to β-amyloid plaques (βA) in the brain, which can promote the loss of cholinergic neurons in the cerebral cortex and in the hippocampus, which explains the cognitive deficiency and memory loss manifesting in the short term in patients undergoing AD (*Velázquez Farmacología Básica y Clínica* 17 ed. Panamericana: Madrid 2005, 329-335). Therefore, traditional pharmacological treatment of AD involves administration of acetylcholinesterase inhibitors (*Rang y Dale Farmacologia 6ª ed. Elsevier: Barcelona* 2008, 515-516), an enzyme which degrades acetylcholine. However, studies have been done which evidence an increasing activity of MAO-B in the brain of patients undergoing certain neurodegenerative disorders such as, for example, PD or AD (*Biochem. Pharmacol.* 38, 555-561, 1989) and new therapeutic expectations have arisen. MAO-B activity increase originates an increase in the reactive oxygen species (ROS) which contribute to oxidative stress and neuron death. Although more studies are required for clarifying the beneficial effects of MAOI-B in neurodegenerative processes such as AD, said effects are related to ROS reduction, which is neurotoxic, and with monoamines increase in the brain of these patients (*Neurotoxicology* 25, 271-277, 2004; *Journal of Neuroscience Research* 79, 172-179, 2005).

Currently, the main therapeutic application of MAOI-B is in PD treatment (*Translational Neurodegeneration* 1:10, 2012; *Translational Neurodegeneration* 2:19, 2013), a neurological disorder which affects motor activity and results from a decrease in striatum dopamine levels, caused by progressive death of nigrostriatal neurons. Although the classical treatment of the PD have been administration of L-dopa (precursor of dopamine) associated to an inhibitor of peripheral dopa decarboxylase enzyme, more recent therapeutic alternatives involve administration of catechol orthomethyl transferase inhibitors (COMT), such as entacapone, and also MAOI-B selective inhibitors, such as selegiline and rasagiline (*Translational Neurodegeneration* 1:10, 2012).

There are several articles and patents describing compounds which act as selective inhibitors of MAO-B and applications thereof in neurodegenerative disorders, such as for example derivatives of coumarin (ES 2343347; *J. Med. Chem.* 54, 7127-7131, 2011) (compound 1, figure 2), γ-chromones (*Bioorg. Med. Chem. Lett.* 20, 2709-2712, 2010; *Bioorg. Med. Chem. Lett.* 21, 707-709, 2011) (compound 2, figure 2), pyrazolines and other diazaheterocycle derivatives (*J. Med. Chem.* 48, 7113-7122, 2005; *Bioorg. Med Chem. Lett* 20, 6479-6482, 2010; *J. Med. Chem.* 49, 3743-3747, 2006; *J. Med Chem.* 50, 5364-5371, 2007) (compounds 3 and 4, figure 2), thiazolyl-hydrazines (*J. Med. Chem.* 53, 6516-6520, 2010; *Arch. Pharm. Chem. Life Sci.* 346, 17-22, 2013) (compound 5, figure 2), dithiolane-thiones (WO2006/089861) (compound 6, figure 2), and amines or amides derived from heterocyclic systems (EP 1524267; WO 2004/007429; EP1524265, *J. Med. Chem.* 50, 922-931, 2007) (compounds 7 and 8, figure 2).

Figure 2 shows a detailed structure of several compounds having MAOI-B activity.

Pyridazine is a diazine which is rare in natural products. However, this heteronucleus is part of a small group of structures known as privileged, due to the capacity thereof of generating compounds being active against several targets, (*Med. Chem. Comun.* 2, 935-941, 2011). Pyridazine derivatives have a wide spectrum of pharmacological activity (cardiotonic, anti-hypertensive, platelet antiaggregate, hypolipidemic, analgesic and anti-inflammatory, antinociceptive, anti-depressant, anxiolytic, GABA antagonist, hypoglycaemic, anti-infectious or antineoplastic, among others), and many of them are analogues to the structure of 3(2H)-pyridazinone (*Progress in Medicinal Chemistry, Elsevier Science Publishers Biomedical Division: Amsterdam* 1990, 1-49; *Progress in Medicinal Chemistry, Elsevier Science Publishers Biomedical Division: Amsterdam* 1992, 141-183; *Med. Chem. Res* 22, 2539-2552, 2013).

The pyridazine ring is present in compounds acting as MAO-B selective inhibitors; these are condensed polycyclic systems (*J. Med. Chem.* 49, 3743-3747, 2006; *J. Med Chem.* 50, 5364-5371, 2007; *J. Med. Chem.* 49, 6264-6272, 2007) (compound 4, figure 2). Furthermore, there are articles and patents referring to simple pyridazine derivatives which act upon other therapeutic targets being efficient in neurodegenerative disorders, such as, for example, agonists of $GABA_A$ receptor (WO 2012/068161; WO 2010/127968) (compound 9, figure 3), agonists of the cannabinoid receptor CB2 (WO 2011/097553) (compound 10, figure 3), activators of glutamate transporter protein (WO 2013/019938) (compound 11, figure 3), modulators of γ-secretase (*Med. Chem. Lett.* 1, 184-187, 2010; *Bioorg. Med Chem. Lett.* 21, 4016-4019, 2011) (compound 12, figure 3), or inhibitors of tau protein oligomerization (*Biochemistry*, 48, 7732-7745, 2009) (compound 13, figure 3), some of which are 3-(2H)-pyridazinone (compounds 10, 12 and 13).

However, 3-(2H)-pyridazinone derivatives which act as selective MAOI-B are not known.

FIG. 3

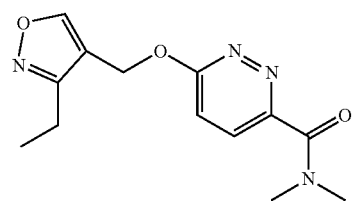

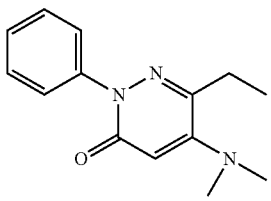

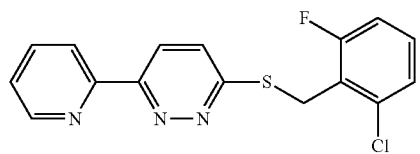

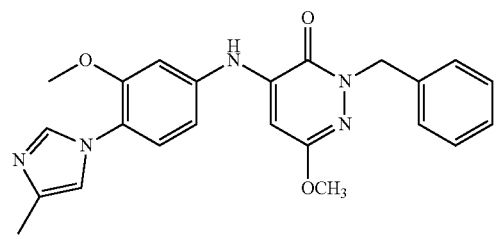

-continued

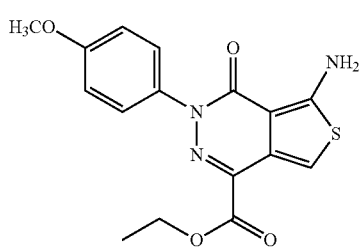

13

The compounds of the present invention lack of structural relationship with those described so far, and behaved as selective inhibitors against MAO-B. These are novel 3-(2H)-pyridazinone derivatives substituted in positions 4, 5 or 6 with dithiocarbamate moieties, bonded to said positions through an alkyl chain of variable length, which selectively inhibit MAO-B activity when the bioactivity thereof is assayed in vitro.

DESCRIPTION OF THE INVENTION

The present invention refers to novel C4-, C5- or C6-substituted pyridazinone derivative compounds having dithiocarbamate moieties, and of general structure I, II and III, respectively, which are selective MAO-B inhibitors in vitro, and to the possible use thereof for preparing medicaments intended to treat disorders derived from MAO-B hyperactivity, particularly degenerative disorders of the central nervous system (CNS), such as Parkinson's disease (PD), Alzheimer's disease (AD) and other dementias.

These are pyridazin-3(2H)-one having dithiocarbamate moieties bonded to position 6 through an alkyl chain of variable length and of the general formula I.

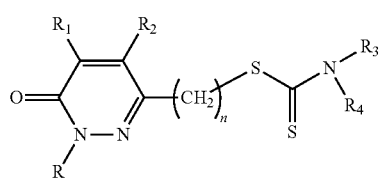

(I)

wherein,
n is an integer number selected from 1, 2, 3, 4, 5, 6, 7, 8;
R is a group selected from: a hydrogen atom, a $C_1$-$C_6$ alkyl group, a $C_1$-$C_6$ carboxyalkyl group, a $C_1$-$C_6$ haloalkyl group, a $C_6$-$C_{12}$ aryl group, a $C_6$-$C_{12}$ aralkyl group, a $C_4$-$C_{12}$ heteroaryl group;
$R^1$ is a group selected from: a hydrogen atom, a $C_1$-$C_6$ alkyl group, a halogen atom,
$R^2$ is a group selected from: a hydrogen atom, a $C_1$-$C_6$ alkyl group, a halogen atom,
$R^3$, $R^4$, being the same or different, are selected from: a hydrogen atom, a $C_1$-$C_6$ alkyl group, saturated $C_1$-$C_6$ heterocycloalkyl group, a $C_6$-$C_{12}$ aryl group, a $C_6$-$C_{12}$ aralkyl group, a $C_4$-$C_{12}$ heteroaryl group,
Or $R^3$ and $R^4$ form a cycle selected from: $C_5$-$C_8$ cycloalkyl, $C_5$-$C_8$ heterocycloalkyl, N-alkyl substituted $C_5$-$C_8$ heterocycloalkyl, N-aryl substituted $C_5$-$C_8$ heterocycloalkyl, N-cycloalkyl substituted $C_5$-$C_8$ heterocycloalkyl, N-aralkyl substituted $C_5$-$C_8$ heterocycloalkyl, N-acyl substituted $C_5$-$C_8$ heterocycloalkyl.

And preferably
R is $CH_3$, phenyl (Ph) or benzyl (Bn).
$R^1$ is H, halogen (Cl, Br, I) or an alkyl chain
$R^2$ is hydrogen (H) or methyl ($CH_3$).
n is optionally 1, 2 or 3.
$R^3$ and $R^4$ may be hydrogen, alkyl groups being the same or different, such as methyl ($CH_3$) or ethyl ($CH_2CH_3$), or, together with the nitrogen atom (N), they may constitute a 5 or 6 membered heterocyclic ring, being aliphatic or incorporating an oxygen atom (O) or a second N atom. This second N atom may be substituted with a linear ($CH_3$, $CH_2CH_3$) or cyclic (cyclopropyl) alkyl group, or with an aryl group (Ph), aralkyl (Bn) or aroyl (benzoyl, Bz).

In a particular aspect, the compounds of the general formula I are represented by the formulae $Ia_1$-$a_{33}$ (table I), $Ib_1$-$b_{33}$ (table II), $Ic_1$-$c_{33}$ (table III) and $Id_1$-$d_{33}$ (table IV), wherein $R^1$ is preferably H.

TABLE I

Ia

| | n = 1 | n = 2 | n = 3 |
|---|---|---|---|
| —N(CH$_3$)$_2$ | Ia$_1$ | Ia$_{12}$ | Ia$_{23}$ |
| —N(CH$_2$CH$_3$)$_2$ | Ia$_2$ | Ia$_{13}$ | Ia$_{24}$ |
| —N⟨pyrrolidine⟩ | Ia$_3$ | Ia$_{14}$ | Ia$_{25}$ |
| —N⟨piperidine⟩ | Ia$_4$ | Ia$_{15}$ | Ia$_{26}$ |
| —N⟨morpholine⟩ | Ia$_5$ | Ia$_{16}$ | Ia$_{27}$ |
| —N⟨N-CH$_3$ piperazine⟩ | Ia$_6$ | Ia$_{17}$ | Ia$_{28}$ |
| —N⟨N-C$_2$H$_5$ piperazine⟩ | Ia$_7$ | Ia$_{18}$ | Ia$_{29}$ |
| —N⟨N-cyclopropyl piperazine⟩ | Ia$_8$ | Ia$_{19}$ | Ia$_{30}$ |
| —N⟨N-Ph piperazine⟩ | Ia$_9$ | Ia$_{20}$ | Ia$_{31}$ |

TABLE I-continued

Ia

[Structure: 1-methyl-6-oxo-pyridazin-3-yl-(CH₂)$_n$-S-C(=S)-NR³R⁴]

| —NR³R⁴ | n = 1 | n = 2 | n = 3 |
|---|---|---|---|
| piperazine-N-Bn | Ia$_{10}$ | Ia$_{21}$ | Ia$_{32}$ |
| piperazine-N-Bz | Ia$_{11}$ | Ia$_{22}$ | Ia$_{33}$ |

TABLE II

Ib

[Structure: 1-phenyl-6-oxo-pyridazin-3-yl-(CH₂)$_n$-S-C(=S)-NR³R⁴]

| —NR³R⁴ | n = 1 | n = 2 | n = 3 |
|---|---|---|---|
| —N(CH$_3$)$_2$ | Ib$_1$ | Ib$_{12}$ | Ib$_{23}$ |
| —N(CH$_2$CH$_3$)$_2$ | Ib$_2$ | Ib$_{13}$ | Ib$_{24}$ |
| pyrrolidine | Ib$_3$ | Ib$_{14}$ | Ib$_{25}$ |
| piperidine | Ib$_4$ | Ib$_{15}$ | Ib$_{26}$ |
| morpholine | Ib$_5$ | Ib$_{16}$ | Ib$_{27}$ |
| piperazine-N-CH$_3$ | Ib$_6$ | Ib$_{17}$ | Ib$_{28}$ |
| piperazine-N-C$_2$H$_5$ | Ib$_7$ | Ib$_{18}$ | Ib$_{29}$ |
| piperazine-N-cyclopropyl | Ib$_8$ | Ib$_{19}$ | Ib$_{30}$ |

TABLE II-continued

Ib

[Structure: 1-phenyl-6-oxo-pyridazin-3-yl-(CH₂)$_n$-S-C(=S)-NR³R⁴]

| —NR³R⁴ | n = 1 | n = 2 | n = 3 |
|---|---|---|---|
| piperazine-N-Ph | Ib$_9$ | Ib$_{20}$ | Ib$_{31}$ |
| piperazine-N-Bn | Ib$_{10}$ | Ib$_{21}$ | Ib$_{32}$ |
| piperazine-N-Bz | Ib$_{11}$ | Ib$_{22}$ | Ib$_{33}$ |

TABLE III

Ic

[Structure: 1-benzyl-6-oxo-pyridazin-3-yl-(CH₂)$_n$-S-C(=S)-NR³R⁴]

| —NR³R⁴ | n = 1 | n = 2 | n = 3 |
|---|---|---|---|
| —N(CH$_3$)$_2$ | Ic$_1$ | Ic$_{12}$ | Ic$_{23}$ |
| —N(CH$_2$CH$_3$)$_2$ | Ic$_2$ | Ic$_{13}$ | Ic$_{24}$ |
| pyrrolidine | Ic$_3$ | Ic$_{14}$ | Ic$_{25}$ |
| piperidine | Ic$_4$ | Ic$_{15}$ | Ic$_{26}$ |
| morpholine | Ic$_5$ | Ic$_{16}$ | Ic$_{27}$ |
| piperazine-N-CH$_3$ | Ic$_6$ | Ic$_{17}$ | Ic$_{28}$ |
| piperazine-N-C$_2$H$_5$ | Ic$_7$ | Ic$_{18}$ | Ic$_{29}$ |

TABLE III-continued

Ic (Structure: pyridazinone with N-Bn, connected via -(CH$_2$)$_n$-S-C(=S)-NR$^3$R$^4$)

$-NR^3R^4$ group:

| $-NR^3R^4$ | n = 1 | n = 2 | n = 3 |
|---|---|---|---|
| piperazinyl-cyclopropyl | Ic$_8$ | Ic$_{19}$ | Ic$_{30}$ |
| piperazinyl-Ph | Ic$_9$ | Ic$_{20}$ | Ic$_{31}$ |
| piperazinyl-Bn | Ic$_{10}$ | Ic$_{21}$ | Ic$_{32}$ |
| piperazinyl-Bz | Ic$_{11}$ | Ic$_{22}$ | Ic$_{33}$ |

TABLE IV

Id (Structure: 4-methyl-pyridazin-6(1H)-one with N-R, 3-CH$_2$-S-C(=S)-NR$^3$R$^4$)

| $-NR^3R^4$ | R = Me | R = Ph | R = Bn |
|---|---|---|---|
| $-N(CH_3)_2$ | Id$_1$ | Id$_{12}$ | Id$_{23}$ |
| $-N(CH_2CH_3)_2$ | Id$_2$ | Id$_{13}$ | Id$_{24}$ |
| pyrrolidinyl | Id$_3$ | Id$_{14}$ | Id$_{25}$ |
| piperidinyl | Id$_4$ | Id$_{15}$ | Id$_{26}$ |
| morpholinyl | Id$_5$ | Id$_{16}$ | Id$_{27}$ |
| 4-methylpiperazinyl | Id$_6$ | Id$_{17}$ | Id$_{28}$ |
| 4-ethylpiperazinyl | Id$_7$ | Id$_{18}$ | Id$_{29}$ |
| 4-cyclopropylpiperazinyl | Id$_8$ | Id$_{19}$ | Id$_{30}$ |
| 4-phenylpiperazinyl | Id$_9$ | Id$_{20}$ | Id$_{31}$ |
| 4-benzylpiperazinyl | Id$_{10}$ | Id$_{21}$ | Id$_{32}$ |
| 4-Bz-piperazinyl | Id$_{11}$ | Id$_{22}$ | Id$_{33}$ |

These are pyridazin-3(2H)-one having dithiocarbamate moieties bonded to position 5 through an alkyl chain of variable length and of general formula II.

II (General formula II: pyridazinone with R$_1$, R$_2$, R substituents and -(CH$_2$)$_n$-S-C(=S)-NR$_3$R$_4$)

wherein,
n is an integer number selected from 1, 2, 3, 4, 5, 6, 7, 8;
R is a group selected from: a hydrogen atom, a $C_1$-$C_6$ alkyl group, a $C_1$-$C_6$ carboxyalkyl group, a $C_1$-$C_6$ haloalkyl group, a $C_6$-$C_{12}$ aryl group, a $C_6$-$C_{12}$ aralkyl group, a $C_4$-$C_{12}$ heteroaryl group;
R$^1$ is a group selected from: a hydrogen atom, a $C_1$-$C_6$ alkyl group, a halogen atom,
R$^2$ is a group selected from: a hydrogen atom, a $C_1$-$C_6$ alkyl group, a halogen atom,
R$^3$, R$^4$, being the same or different, are selected from: a hydrogen atom, a $C_1$-$C_6$ alkyl group, saturated $C_1$-$C_6$ heterocycloalkyl group, a $C_6$-$C_{12}$ aryl group, a $C_6$-$C_{12}$ aralkyl group, a $C_4$-$C_{12}$ heteroaryl group,
Or R$^3$ and R$^4$ form a cycle selected from: $C_5$-$C_8$ cycloalkyl, $C_5$-$C_8$ heterocycloalkyl, N-alkyl substituted $C_5$-$C_8$ heterocycloalkyl, N-aryl substituted $C_5$-$C_8$ heterocycloalkyl, N-cycloalkyl substituted $C_5$-$C_8$ heterocycloalkyl, N-aralkyl substituted $C_5$-$C_8$ heterocycloalkyl, N-acyl substituted $C_5$-$C_8$ heterocycloalkyl.

And preferably

R is $CH_3$, phenyl (Ph) or benzyl (Bn).

$R^1$ is H, halogen (Cl, Br, I) or an alkyl chain $R^2$ is hydrogen (H).

n is optionally 1, 2 or 3.

$R^3$ and $R^4$ may be hydrogen, alkyl groups being the same or different, such as methyl ($CH_3$) or ethyl ($CH_2CH_3$), or, together with the nitrogen atom (N), they may constitute a 5 or 6 membered heterocyclic ring, being aliphatic or incorporating an oxygen atom (O) or a second N atom. This second N atom may be substituted with a linear ($CH_3$, $CH_2CH_3$) or cyclic (cyclopropyl) alkyl group, or with an aryl group (Ph), aralkyl (Bn) or aroyl (benzoyl, Bz).

In a particular aspect, the compounds of general formula II are represented by formulae $IIa_1$-$a_{33}$ (table V), $IIb_1$-$b_{33}$ (table VI), $IIc_1$-$c_{33}$ (table VII) where $R^1$ and $R^2$ are preferably H.

TABLE V

IIa

[Structure: pyridazinone with $H_3C$-N, substituent $-(CH_2)_n-S-C(=S)-N(R_3)(R_4)$]

$-N(R^3)(R^4)$

| $-N(R^3)(R^4)$ | n = 1 | n = 2 | n = 3 |
|---|---|---|---|
| —N(CH$_3$)$_2$ | IIa$_1$ | IIa$_{12}$ | IIa$_{23}$ |
| —N(CH$_2$CH$_3$)$_2$ | IIa$_2$ | IIa$_{13}$ | IIa$_{24}$ |
| —N(pyrrolidinyl) | IIa$_3$ | IIa$_{14}$ | IIa$_{25}$ |
| —N(piperidinyl) | IIa$_4$ | IIa$_{15}$ | IIa$_{26}$ |
| —N(morpholinyl) | IIa$_5$ | IIa$_{16}$ | IIa$_{27}$ |
| —N(4-methylpiperazinyl) | IIa$_6$ | IIa$_{17}$ | IIa$_{28}$ |
| —N(4-ethylpiperazinyl) | IIa$_7$ | IIa$_{18}$ | IIa$_{29}$ |
| —N(4-cyclopropylpiperazinyl) | IIa$_8$ | IIa$_{19}$ | IIa$_{30}$ |

TABLE V-continued

IIa

| $-N(R^3)(R^4)$ | n = 1 | n = 2 | n = 3 |
|---|---|---|---|
| —N(4-phenylpiperazinyl) | IIa$_9$ | IIa$_{20}$ | IIa$_{31}$ |
| —N(4-benzylpiperazinyl) | IIa$_{10}$ | IIa$_{21}$ | IIa$_{32}$ |
| —N(4-benzoylpiperazinyl) | IIa$_{11}$ | IIa$_{22}$ | IIa$_{33}$ |

TABLE VI

IIb

[Structure: pyridazinone with Ph-N, substituent $-(CH_2)_n-S-C(=S)-N(R_3)(R_4)$]

| $-N(R^3)(R^4)$ | n = 1 | n = 2 | n = 3 |
|---|---|---|---|
| —N(CH$_3$)$_2$ | IIb$_1$ | IIb$_{12}$ | IIb$_{23}$ |
| —N(CH$_2$CH$_3$)$_2$ | IIb$_2$ | IIb$_{13}$ | IIb$_{24}$ |
| —N(pyrrolidinyl) | IIb$_3$ | IIb$_{14}$ | IIb$_{25}$ |
| —N(piperidinyl) | IIb$_4$ | IIb$_{15}$ | IIb$_{26}$ |
| —N(morpholinyl) | IIb$_5$ | IIb$_{16}$ | IIb$_{27}$ |
| —N(4-methylpiperazinyl) | IIb$_6$ | IIb$_{17}$ | IIb$_{28}$ |

TABLE VI-continued

IIb

[Structure: pyridazin-3(2H)-one with N-Ph, bearing -(CH2)n-S-C(=S)-N(R3)(R4) at position 4]

−N(R3)(R4):

| R3R4-amine | n = 1 | n = 2 | n = 3 |
|---|---|---|---|
| −N(piperazinyl)−C2H5 | IIb7 | IIb18 | IIb29 |
| −N(piperazinyl)−cyclopropyl | IIb8 | IIb19 | IIb30 |
| −N(piperazinyl)−Ph | IIb9 | IIb20 | IIb31 |
| −N(piperazinyl)−Bn | IIb10 | IIb21 | IIb32 |
| −N(piperazinyl)−Bz | IIb11 | IIb22 | IIb33 |

TABLE VII

IIc

[Structure: pyridazin-3(2H)-one with N-Bn, bearing -(CH2)n-S-C(=S)-N(R3)(R4) at position 4]

−N(R3)(R4):

| R3R4-amine | n = 1 | n = 2 | n = 3 |
|---|---|---|---|
| −N(CH3)2 | IIc1 | IIc12 | IIc23 |
| −N(CH2CH3)2 | IIc2 | IIc13 | IIc24 |
| −pyrrolidinyl | IIc3 | IIc14 | IIc25 |
| −piperidinyl | IIc4 | IIc15 | IIc26 |

TABLE VII-continued

IIc

[Structure: pyridazin-3(2H)-one with N-Bn, bearing -(CH2)n-S-C(=S)-N(R3)(R4) at position 4]

−N(R3)(R4):

| R3R4-amine | n = 1 | n = 2 | n = 3 |
|---|---|---|---|
| −morpholinyl | IIc5 | IIc16 | IIc27 |
| −N(piperazinyl)−CH3 | IIc6 | IIc17 | IIc28 |
| −N(piperazinyl)−C2H5 | IIc7 | IIc18 | IIc29 |
| −N(piperazinyl)−cyclopropyl | IIc8 | IIc19 | IIc30 |
| −N(piperazinyl)−Ph | IIc9 | IIc20 | IIc31 |
| −N(piperazinyl)−Bn | IIc10 | IIc21 | IIc32 |
| −N(piperazinyl)−Bz | IIc11 | IIc22 | IIc33 |

These are pyridazin-3(2H)-one representing dithiocarbamate moieties bonded to position 4 through an alkyl chain of variable length and of the general formula III.

III

[Structure: general formula III — pyridazin-3(2H)-one with N-R, R2 at position 3, R1 at position 4, and -(CH2)n-S-C(=S)-N(R3)(R4) substituent]

wherein,
n is an integer number selected from 1, 2, 3, 4, 5, 6, 7, 8;
R is a group selected from: a hydrogen atom, a $C_1$-$C_6$ alkyl group, a $C_1$-$C_6$ carboxyalkyl group, a $C_1$-$C_6$ haloalkyl group, a $C_6$-$C_{12}$ aryl group, a $C_6$-$C_{12}$ aralkyl group, a $C_4$-$C_{12}$ heteroaryl group;

$R^1$ is a group selected from: a hydrogen atom, a $C_1$-$C_6$ alkyl group, a halogen atom, $R^2$ is a group selected from: a hydrogen atom, a $C_1$-$C_6$ alkyl group, a halogen atom, $R^3$, $R^4$, being the same or different, are selected from: a hydrogen atom, a $C_1$-$C_6$ alkyl group, saturated $C_1$-$C_6$ heterocycloalkyl group, a $C_6$-$C_{12}$ aryl group, a $C_6$-$C_{12}$ aralkyl group, a $C_4$-$C_{12}$ heteroaryl group, Or $R^3$ and $R^4$ form a cycle selected from: $C_5$-$C_8$ cycloalkyl, $C_5$-$C_8$ heterocycloalkyl, N-alkyl substituted $C_5$-$C_8$ heterocycloalkyl, N-aryl substituted $C_5$-$C_8$ heterocycloalkyl, N-cycloalkyl substituted $C_5$-$C_8$ heterocycloalkyl, N-aralkyl substituted $C_5$-$C_8$ heterocycloalkyl, N-acyl substituted $C_5$-$C_8$ heterocycloalkyl.

And preferably

R is $CH_3$, phenyl (Ph) or benzyl (Bn).

$R^1$ is H, halogen (Cl, Br, I) or an alkyl chain $R^2$ is hydrogen (H).

n is optionally 1, 2 or 3.

$R^3$ and $R^4$ may be hydrogen, alkyl groups being the same or different, such as methyl ($CH_3$) or ethyl ($CH_2CH_3$), or, together with the nitrogen atom (N), they may constitute a 5 or 6 membered heterocyclic ring, being aliphatic or incorporating an oxygen atom (O) or a second N atom. This second N atom may be substituted with a linear ($CH_3$, $CH_2CH_3$) or cyclic (cyclopropyl) alkyl group, or with an aryl group (Ph), aralkyl (Bn) or aroyl (benzoyl, Bz).

In a particular aspect, the compounds of the general formula I are represented by formulae $IIIa_1$-$a_{33}$ (table VIII), $IIIb_1$-$b_{33}$ (table IX), $IIIc_1$-$c_{33}$ (table X), where $R^1$ and $R^2$ are preferably H.

TABLE VIII

IIIa

| $-N(R^3)(R^4)$ | n = 1 | n = 2 | n = 3 |
|---|---|---|---|
| $-N(CH_3)_2$ | $IIIa_1$ | $IIIa_{12}$ | $IIIa_{23}$ |
| $-N(CH_2CH_3)_2$ | $IIIa_2$ | $IIIa_{13}$ | $IIIa_{24}$ |
| pyrrolidinyl | $IIIa_3$ | $IIIa_{14}$ | $IIIa_{25}$ |
| piperidinyl | $IIIa_4$ | $IIIa_{15}$ | $IIIa_{26}$ |
| morpholinyl | $IIIa_5$ | $IIIa_{16}$ | $IIIa_{27}$ |
| 4-methylpiperazinyl | $IIIa_6$ | $IIIa_{17}$ | $IIIa_{28}$ |
| 4-ethylpiperazinyl | $IIIa_7$ | $IIIa_{18}$ | $IIIa_{29}$ |
| 4-cyclopropylpiperazinyl | $IIIa_8$ | $IIIa_{19}$ | $IIIa_{30}$ |
| 4-phenylpiperazinyl | $IIIa_9$ | $IIIa_{20}$ | $IIIa_{31}$ |
| 4-benzylpiperazinyl | $IIIa_{10}$ | $IIIa_{21}$ | $IIIa_{32}$ |
| 4-benzoylpiperazinyl | $IIIa_{11}$ | $IIIa_{22}$ | $IIIa_{33}$ |

TABLE IX

IIIb

| $-N(R^3)(R^4)$ | n = 1 | n = 2 | n = 3 |
|---|---|---|---|
| $-N(CH_3)_2$ | $IIIb_1$ | $IIIb_{12}$ | $IIIb_{23}$ |
| $-N(CH_2CH_3)_2$ | $IIIb_2$ | $IIIb_{13}$ | $IIIb_{24}$ |
| pyrrolidinyl | $IIIb_3$ | $IIIb_{14}$ | $IIIb_{25}$ |
| piperidinyl | $IIIb_4$ | $IIIb_{15}$ | $IIIb_{26}$ |

TABLE IX-continued

IIIb

[Structure: Pyridazinone with N-Ph, C=O, and S-C(=S)-N(R3)(R4) substituent with (CH2)n linker]

| –N(R3)(R4) | n = 1 | n = 2 | n = 3 |
|---|---|---|---|
| morpholine (–N(CH2CH2)2O) | IIIb$_5$ | IIIb$_{16}$ | IIIb$_{27}$ |
| 4-methylpiperazine (–N(CH2CH2)2N–CH3) | IIIb$_6$ | IIIb$_{17}$ | IIIb$_{28}$ |
| 4-ethylpiperazine (–N(CH2CH2)2N–C2H5) | IIIb$_7$ | IIIb$_{18}$ | IIIb$_{29}$ |
| 4-cyclopropylpiperazine | IIIb$_8$ | IIIb$_{19}$ | IIIb$_{30}$ |
| 4-phenylpiperazine (–N(CH2CH2)2N–Ph) | IIIb$_9$ | IIIb$_{20}$ | IIIb$_{31}$ |
| 4-benzylpiperazine (–N(CH2CH2)2N–Bn) | IIIb$_{10}$ | IIIb$_{21}$ | IIIb$_{32}$ |
| 4-benzoylpiperazine (–N(CH2CH2)2N–Bz) | IIIb$_{11}$ | IIIb$_{22}$ | IIIb$_{33}$ |

TABLE X

IIIc

[Structure: Pyridazinone with N-Bn, C=O, and S-C(=S)-N(R3)(R4) substituent with (CH2)n linker]

| –N(R3)(R4) | n = 1 | n = 2 | n = 3 |
|---|---|---|---|
| –N(CH3)2 | IIIc$_1$ | IIIc$_{12}$ | IIIc$_{23}$ |
| –N(CH2CH3)2 | IIIc$_2$ | IIIc$_{13}$ | IIIc$_{24}$ |
| pyrrolidine | IIIc$_3$ | IIIc$_{14}$ | IIIc$_{25}$ |
| piperidine | IIIc$_4$ | IIIc$_{15}$ | IIIc$_{26}$ |
| morpholine | IIIc$_5$ | IIIc$_{16}$ | IIIc$_{27}$ |
| 4-methylpiperazine | IIIc$_6$ | IIIc$_{17}$ | IIIc$_{28}$ |
| 4-ethylpiperazine | IIIc$_7$ | IIIc$_{18}$ | IIIc$_{29}$ |
| 4-cyclopropylpiperazine | IIIc$_8$ | IIIc$_{19}$ | IIIc$_{30}$ |
| 4-phenylpiperazine | IIIc$_9$ | IIIc$_{20}$ | IIIc$_{31}$ |
| 4-benzylpiperazine | IIIc$_{10}$ | IIIc$_{21}$ | IIIc$_{32}$ |
| 4-benzoylpiperazine | IIIc$_{11}$ | IIIc$_{22}$ | IIIc$_{33}$ |

In another aspect, the invention refers to a medicament comprising a compound of formula (I), (II) or (III), as it has been described above, or a salt thereof in a pharmaceutically acceptable carrier, having one or more pharmaceutically acceptable excipients.

In a particular embodiment, said medicament also comprises one or more additional therapeutic agents.

Synthesis

The compounds Ia-d, IIa-c and IIIa-c could be obtained by means of any known chemical process being applicable to similar compounds.

In another aspect, the invention refers to a method for the synthesis of a compound of formula (I), (II) or (III), as it has been described above, characterized in that it comprises at least a stage, wherein the 6(5)(4)-bromoalkyl-3(2H)-pyridazinone of formula (IV), (IX) o (XIII), a secondary amine of formula V and carbon disulphide ($CS_2$) react in the presence of a base in a solvent at room temperature.

The compounds Ia-d of the general formula I were obtained by means of a multi-component reaction between the 6-bromoalkyl-3(2H)-pyridazinones of formula IV, a secondary amine of formula V and carbon disulphide ($CS_2$) in the presence of anhydrous potassium phosphate ($K_3PO_4$) as an example of a base, in dimethylformamide (DMF) as an example of solvent, and at room temperature (RT), such as it is shown in scheme 1.

Scheme 1

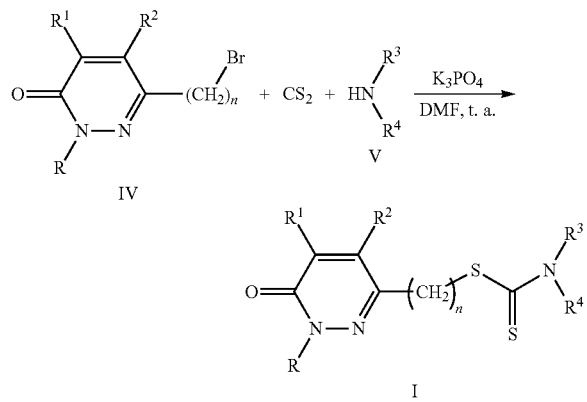

Wherein R, $R^1$, $R^2$, $R^3$, $R^4$ and n are as described above for the compounds of formula I.

$CS_2$ and amines of formula V are commercial compounds, while the 6-bromoalkyl-3(2H)-pyridazinones of formula IV can be obtained from 6-hydroxyalkyl-3(2H)-pyridazinones of formula VI, where R, $R^1$, $R^2$ and n are as described above, by carbon tetrabromide bromination ($CBr_4$) and triphenylphosphine ($PPh_3$) or with N-bromosuccinimide (NBS) and $PPh_3$, adapting standard procedures (*J. Heterocyclic Chem.* 36, 985-990, 1999; *Tetrahedron* 50, 13575-13682, 1994).

Precursors of structure VI can be prepared in two stages (scheme 2) from 5-(tert-butyldiphenylsyliloxyalkyl)-5-hydroxy(methoxy)-5H-furan-2-ones of structure VII, wherein $R^1$, $R^2$ and n are as described above, and similarly, as described in the bibliography (*Bioorg. Med. Chem. Lett.* 20, 6624-6627, 2010; *Magn. Reson. Chem.*, 49, 437-442, 2011). A first reaction of the furanones VII with methylhydrazine ($CH_3NHNH_2$), phenylhydrazine ($PhNHNH_2$) or benzylhydrazine ($BnNHNH_2$) in ethanol (EtOH), provides the 6-(tert-butyldiphenylsyliloxyalkyl)-3(2H)-pyridazinones of structure VIII, wherein R, $R^1$, $R^2$ and n are as described above, which transform into the 6-hydroxyalkyl-3(2H)-pyridazinones VI by reaction with tetrabutylammonium fluoride (TBAF) in tetrahydrofuran (THF).

Scheme 2

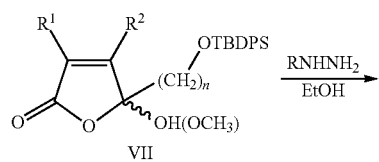

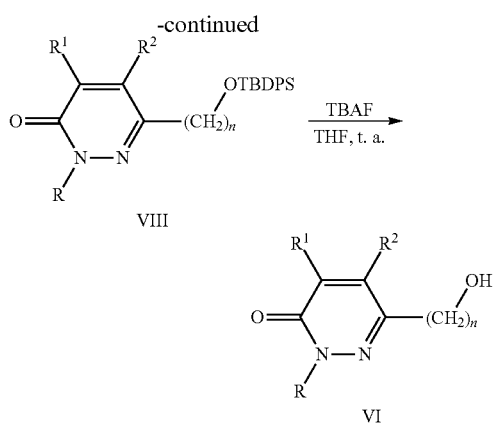

Furanones of structure VII can be prepared from the corresponding 2-alkylfuranes by oxidation with singlet oxygen, in a manner being analogous to that described in the bibliography (*Tetrahedron Lett.* 45, 5207-5209, 2004; *Bioorg. Med. Chem. Lett.* 20, 6624-6627, 2010; *Magn. Reson. Chem.*, 49, 437-442, 2011).

Compounds IIa-c of general formula II were obtained by multicomponent reaction between 5-bromoalkyl-3(2H)-pyridazinones of formula IX, a secondary amine of formula V and carbon disulphide ($CS_2$) in the presence of anhydrous potassium phosphate ($K_3PO_4$), in dimethylformamide (DMF) and at room temperature (RT), as it is shown in scheme 3.

Scheme 3

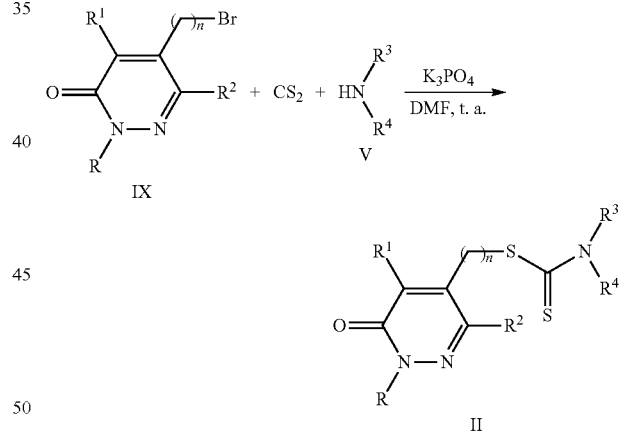

Wherein R, $R^1$, $R^2$, $R^3$, $R^4$ and n are as described above for the compounds of formula I.

$CS_2$ and amines of formula V are commercial compounds, whereas 5-bromoalkyl-3(2H)-pyridazinones of formula IX can be obtained from 5-hydroxyalkyl-3(2H)-pyridazinones of formula X, wherein R, $R^1$, $R^2$ and n are as described above, by carbon tetrabromide bromination ($CBr_4$) and triphenylphosphine ($PPh_3$) or with N-bromosuccinimide (NBS) and $PPh_3$, adapting standard procedures (*J. Heterocyclic Chem.* 36, 985-990, 1999; *Tetrahedron* 50, 13575-13682, 1994).

Precursors of structure X can be prepared in two stages (scheme 4) from 4-(tert-butyldiphenylsyliloxyalkyl)-5-hydroxy-5H-furan-2-ones of structure XI, wherein $R^1$, $R^2$ and n are as described above, and similarly, as described in the bibliography (*Bioorg. Med. Chem. Lett.* 20, 6624-6627, 2010; *Magn. Reson. Chem.,* 49, 437-442, 2011). A first reaction of the furanones XI with methylhydrazine (CH$_3$NHNH$_2$), phenylhydrazine (PhNHNH$_2$) or benzylhydrazine (BnNHNH$_2$) in ethanol (EtOH), provides the 5-(tert-butyldiphenylsyliloxyalkyl)-3(2H)-pyridazinones of structure XII, wherein R, R$^1$, R$^2$ and n are as described above, which transform into the 5-hydroxyalkyl-3(2H)-pyridazinones X by reaction with tetrabutylammonium fluoride (TBAF) in tetrahydrofuran (THF).

Scheme 4

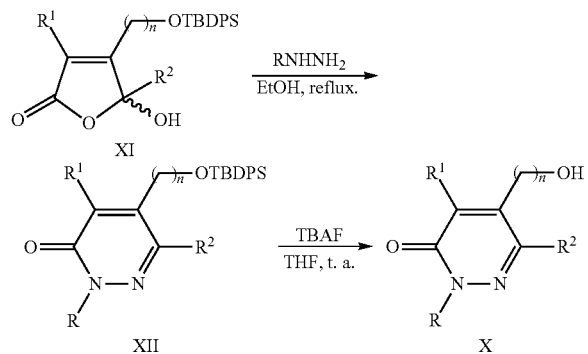

Furanones of structure XI can be prepared from the corresponding 3-alkylfuranes by oxidation with singlet oxygen, in a manner being analogous to that described in the bibliography (*Tetrahedron Lett.* 45, 5207-5209, 2004; *Bioorg. Med. Chem. Lett.* 20, 6624-6627, 2010; *Magn. Reson. Chem.,* 49, 437-442, 2011).

Compounds IIIa-c of general formula III were obtained by multicomponent reaction between 4-bromoalkyl-3(2H)-pyridazinones of formula XIII, a secondary amine of formula V and carbon disulphide (CS$_2$) in the presence of anhydrous potassium phosphate (K$_3$PO$_4$), in dimethylformamide (DMF) and at room temperature (RT), as it is shown in scheme 5.

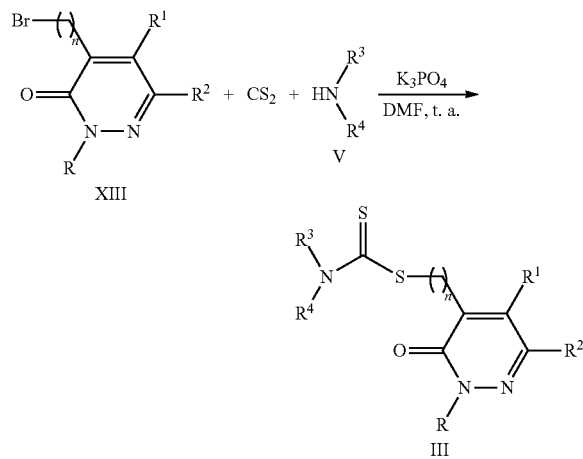

Where R, R$^1$, R$^2$, R$^3$, R$^4$ and n, are as described above for the compounds of formula III.

CS$_2$ and amines of formula V are commercial compounds, whereas 4-bromoalkyl-3(2H)-pyridazinones of formula XIII can be obtained from 4-hydroxyalkyl-3(2H)-pyridazinones of formula XIV, wherein R, R$^1$, R$^2$ and n are as described above, by carbon tetrabromide bromination (CBr$_4$) and triphenylphosphine (PPh$_3$) or with N-bromosuccinimide (NBS) and PPh$_3$, adapting standard procedures (*J. Heterocyclic Chem.* 36, 985-990, 1999; *Tetrahedron* 50, 13575-13682, 1994).

Precursors of structure XIV can be prepared in two stages (scheme 6) from 3-(tert-butyldiphenylsyliloxyalkyl)-5-hydroxy-5H-furan-2-ones of structure XV, wherein R$^1$, R$^2$ and n are as described above, and similarly, as described in the bibliography (*Bioorg. Med. Chem. Lett.* 20, 6624-6627, 2010; *Magn. Reson. Chem.,* 49, 437-442, 2011). A first reaction of the furanones XV with methylhydrazine (CH$_3$NHNH$_2$), phenylhydrazine (PhNHNH$_2$) or benzylhydrazine (BnNHNH$_2$) in ethanol (EtOH), provides the 5-(tert-butyldiphenylsyliloxyalkyl)-3(2H)-pyridazinones of structure XVI, wherein R, R$^1$, R$^2$ and n are as described above, which transform into the 5-hydroxyalkyl-3(2H)-pyridazinones XIV by reaction with tetrabutylammonium fluoride (TBAF) in tetrahydrofuran (THF).

Scheme 6

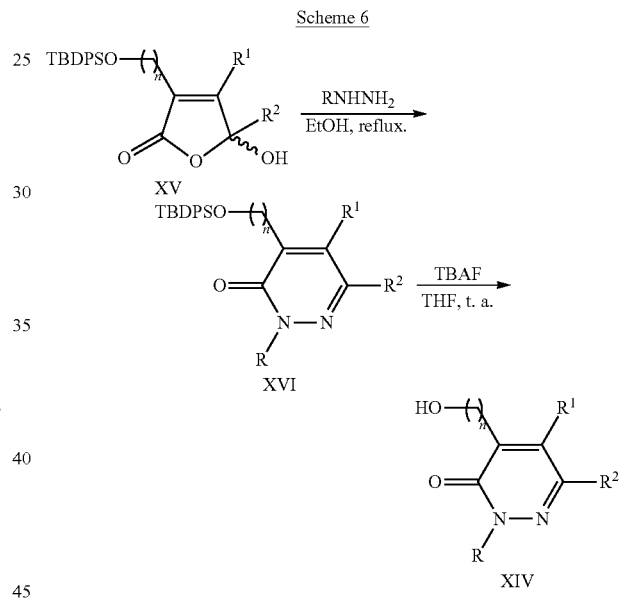

Furanones of structure XV can be prepared from the corresponding 3-alkylfuranes by oxidation with singlet oxygen, in a manner being analogous to that described in the bibliography (*Tetrahedron Lett.* 45, 5207-5209, 2004; *Bioorg. Med. Chem. Lett.* 20, 6624-6627, 2010; *Magn. Reson. Chem.,* 49, 437-442, 2011).

Compounds of formula Ia-d, IIa-c and IIa-c selectively inhibit MAO isoform B and may be used for preparing medicaments intended to treat disorders derived from MAO-B hyperactivity, as degenerative disorders of the central nervous system (CNS), such as Parkinson's disease (PD), Alzheimer's disease (AD) and other dementias.

Some representative compounds of formula Ia-d, IIa-c and IIIa-c to which the present invention refer to, are the following,
a)  1,4-dimethyl-6-oxo-1,6-dihydropyridazin-3-ylmethyl N,N-diethyldithiocarbamate (Id$_2$).
b)  1,4-dimethyl-6-oxo-1,6-dihydropyridazin-3-ylmethyl Pyrrolidin-1-ylcarbodithioate (Id$_3$).
c)  1,4-dimethyl-6-oxo-1,6-dihydropyridazin-3-ylmethyl Piperidin-1-ylcarbodithioate (Id$_4$).

d) 1,4-dimethyl-6-oxo-1,6-dihydropyridazin-3-ylmethyl morpholin-4-ylcarbodithioate ($Id_5$).
e) 1,4-dimethyl-6-oxo-1,6-dihydropyridazin-3-ylmethyl 4-benzoylpiperazin-1-ylcarbodithioate ($Id_{11}$).
f) 2-(1-methyl-6-oxo-1,6-dihydropyridazin-3-yl)ethyl Piperidin-1-ylcarbodithioate ($Ia_{15}$).
g) 3-(1-methyl-6-oxo-1,6-dihydropyridazin-3-yl)propyl Pyrrolidin-1-ylcarbodithioate ($Ia_{25}$).
h) 1-benzyl-6-oxo-1,6-dihydropyridazin-4-ylmethyl N,N-diethyldithiocarbamate ($IIc_2$).
i) 1-benzyl-6-oxo-1,6-dihydropyridazin-4-ylmethyl Pyrrolidin-1-ylcarbodithioate ($IIc_3$).
j) 1-benzyl-6-oxo-1,6-dihydropyridazin-4-ylmethyl Piperidin-1-ylcarbodithioate ($IIc_4$).
k) 1-benzyl-6-oxo-1,6-dihydropyridazin-4-ylmethyl Morpholin-4-ylcarbodithioate ($IIc_5$).
l) 1-benzyl-6-oxo-1,6-dihydropyridazin-4-ylmethyl 4-benzoylpiperazin-1-ylcarbodithioate ($IIc_{11}$).
m) 1-benzyl-6-oxo-1,6-dihydropyridazin-5-ylmethyl Pyrrolidin-1-ylcarbodithioate ($IIIc_3$).
n) 1-benzyl-6-oxo-1,6-dihydropyridazin-5-ylmethyl Morpholin-4-ylcarbodithioate ($IIIc_5$).
o) 1-benzyl-6-oxo-1,6-dihydropyridazin-5-ylmethyl 4-benzoylpiperazin-1-ylcarbodithioate ($IIIc_{11}$).

EXAMPLES

The examples given below should be considered as a way of providing a better understanding of the present invention, without being limitative thereof.

General Procedures

Proton nuclear magnetic resonance spectra ($^1$H NMR) are in all cases according to the structures disclosed. The $^1$H NMRs were registered in the Bruker 400 DPX and Bruker ARX 400 spectrophotometer, using deuterated chloroform ($CDCl_3$) or deuterated methanol ($CD_3OD$). Chemical shifts are expressed in δ units, in parts per million (ppm), relative to tetramethylsilane (TMS), coupling constants (J) are indicated in Hertzs (Hz), and multiplicity as follows: s, singlet; d, doublet; t, triplet; m, multiplet. High resolution mass spectrometry (HRMS) was performed in a Bruker Microtof Focus spectrometer, using electrospray ionization (ESI) or electron impact ionization (EI).

Reactions under inert atmosphere were performed under argon (Ar) atmosphere. All the commercial reagents were directly taken from the bottles provided by the supplier and were used without being purified. Organic solvents were dried by means of standard procedures (*Vogel's Textbook of Practical Organic Chemistry 5th ed. Longman Scientific and Technical: London* 1989; Perrin, D. D., Armarego, W. L. F. *Purification of Laboratory Chemicals*, 6th ed. Butterworth-Heineman Ltd.: Oxford 2008) and were immediately distilled before being used. Reaction development was assessed by thin layer chromatography, using silica gel plates (Merck 60F254), which were visualized by UV light and developed by means of a dissolution containing 3 g of potassium permanganate ($KMnO_4$), 20 g of potassium carbonate ($K_2CO_3$), 5 mL of 5% sodium hydroxide dissolution (NaOH 5%) and 300 mL of water ($H_2O$). The products were purified by pressure column chromatography on silica gel, Merck (230-400 mesh).

Example 1

Preparation of 1,4-dimethyl-6-oxo-1,6-dihydropyridazin-3-ylmethyl N,N-diethyldithiocarbamate ($Id_2$)

A solution of 5-(tert-butyldiphenylsyliloxymethyl)-5-hydroxy-4-methyl-5H-furan-2-one VIId (212 mg, 0.554 mmol) in absolute EtOH (4 mL), was added at room temperature (RT), a $CH_3NHNH_2$ solution (0.06 mL, 1.108 mmol) in absolute EtOH (1 mL). The reaction mixture was stirred at reflux for 18 hours. Once the reaction was finished, and once the resulting solution was cooled, the solvent was removed under vacuum and the residue obtained was purified by column chromatography on silica gel, using hexane/ethyl acetate (3:1) as eluent, thus obtaining 6-(tert-butyldiphenylsyliloxymethyl)-2,5-dimethyl-3(2H)-pyridazinone $VIIId_f$ (313 mg, 52%). EMAR (ESI): m/z calculated for $C_{23}H_{29}N_2O_2Si$ [M+H]$^+$, 393.19983; found 393.19928.

$^1$H NMR (CDCl$_3$) δ: 7.68 (m, 4H,), 7.67 (m, 6H,), 6.70 (d, 1H, J=1.1 Hz), 4.64 (s, 2H), 3.62 (s, 3H,), 2.34 (d, 3H, J=1.1 Hz), 1.01 (s, 9H).

A solution of the compound $VIIId_f$ (74 mg, 0.188 mmol) in THF (4 mL), was added at RT, and under argon (Ar) atmosphere, a 1M TBAF solution in THF (0.2 mL, 0.188 mmol). The reaction mixture was kept under stirring, at RT and under Ar atmosphere for 15 minutes. Once the reaction was finished, it was added some drops of saturated $NaHCO_3$ solution, stirring was kept for 15 additional minutes and then it was dried with anhydrous $Na_2SO_4$. The resulting suspension was filtered and the filtrate was concentrated to dryness under vacuum. The residue obtained was purified by column chromatography on silica gel, using ethyl acetate/methanol (9.5:0.5) as eluent, obtaining 6-hydroxymethyl-2,5-dimethyl-3(2H)-pyridazinone $VId_f$ (26 mg, 86%). EMAR (EI): m/z calculated for $C_7H_{10}N_2O_2$[M]$^+$, 154.0742, found 154.0735.

$^1$H NMR (CDCl$_3$) δ: 6.70 (d, 1H, J=1.1 Hz), 4.58 (s, 2H), 3.73 (s, 3H), 2.21 (d, 3H, J=1.1 Hz).

A solution of the compound $VId_f$ (48 mg, 0.311 mmol) in $CH_2Cl_2$ (8 mL) was successively added $CBr_4$ (207 mg, 0.623 mmol) and $PPh_3$ (163 mg 0.623 mmol). The reaction mixture was kept under stirring at reflux, under Ar atmosphere for 6 hours. Once the reaction was finished, and once the resulting solution was cooled, it was treated with a saturated $NaHCO_3$ solution (2 mL), extracted with $CH_2Cl_2$ (3×5 mL) and the organic extract was dried over anhydrous $Na_2SO_4$. The resulting suspension was filtered and the filtrate was vacuum concentrated. The residue obtained was purified by column chromatography on silica gel, using ethyl acetate/methanol (8.5:1.5) as eluent, thus obtaining 6-bromomethyl-2,5-dimethyl-3(2H)-pyridazinone $IVd_f$ (65 mg, 96%). EMAR (ESI): m/z calculated for $C_7H_{10}BrN_2O$, 216.99710 [M+H]$^+$, found 216.99627.

$^1$H NMR (CDCl$_3$) δ:6.73 (m, 1H), 4.37 (s, 2H), 3.74 (s, 3H), 2.32 (d, 3H, J=1.1 Hz).

A diethylamine solution (8 μL, 0.077 mmol) in DMF (1 mL), was added $CS_2$ (9 μL, 0.141 mmol) and $K_3PO_4$ (16 mg, 0.077 mmol). The mixture obtained was stirred at RT and under Ar atmosphere for 30 minutes. Then, a solution of the compound $IVd_f$ (11 mg, 0.051 mmol) in DMF (1 mL) was added and stirring was kept under the same conditions for 22 hours. Then, the reaction mixture was treated with $H_2O$ (0.5 mL) and was concentrated to dryness under vacuum. The residue obtained was purified by column chromatography on silica gel (eluent: hexane/ethyl acetate 3:1 and 1:3) thus obtaining the compound $Id_2$ (14 mg, 97%). EMAR (ESI): m/z [M+H]$^+$ calculated for $C_{12}H_{20}N_3OS_2$, 286.10423, found 286.10546.

$^1$H NMR (CDCl$_3$) δ: 6.69 (s, 1H), 4.52 (s, 2H), 4.03 (c, 2H, J=7.0 Hz), 3.72 (s, 3H), 3.65 (c, 2H, J=7.0 Hz), 2.26 (s, 3H), 1.28 (m, 6H).

Example 2

Preparation of 1,4-dimethyl-6-oxo-1,6-dihydro-pyridazin-3-ylmethyl Pyrrolidin-1-ylcarbodithioate ($Id_3$)

According to the procedure described for obtaining the compound $Id_2$, a solution of pyrrolidine (8 µL, 0.096 mmol), $CS_2$ (11 µL, 0.175 mmol) and $K_3PO_4$ (20 mg, 0.096 mmol) in DMF (1 mL) was treated with a solution of the compound $IVd_I$ (10 mg, 0.046 mmol) in DMF (1 mL). The residue obtained was purified by column chromatography on silica gel (eluent: hexane/ethyl acetate 3:1 and hexane/ethyl acetate 1:3), obtaining the compound $Id_3$ (13 mg, 100%). EMAR (ESI): m/z calculated for $C_{12}H_{18}N_3OS_2$, 284.08858 [M+H]$^+$, found 284.08856.

$^1$H NMR (CDCl$_3$) δ: 6.69 (m, 1H), 4.55 (s, 2H), 3.94 (t, 2H, J=6.9 Hz), 3.72 (s, 3H), 3.65 (t, 2H, J=6.9 Hz), 2.26 (d, 3H, J=1.1 Hz), 2.08 (m, 2H), 1.99 (m, 2H).

Example 3

Preparation of 1,4-dimethyl-6-oxo-1,6-dihydro-pyridazin-3-ylmethyl Piperidin-1-ylcarbodithioate ($Id_4$)

According to the procedure described for obtaining the compound $Id_2$, a solution of piperidine (8 µL, 0.081 mmol), $CS_2$ (9 µL, 0.147 mmol) and $K_3PO_4$ (17 mg, 0.081 mmol) in DMF (1 mL) was treated with a solution of the compound $IVd_I$ (15 mg, 0.069 mmol) in DMF (1 mL). The residue obtained was purified by column chromatography on silica gel (eluent: hexane/ethyl acetate 3:1, 1:1, 1:3 and 1:4), obtaining the compound $Id_4$ (19 mg, 95%). EMAR (ESI): m/z calculated for $C_{13}H_{20}N_3OS_2$, 298.10423 [M+H]$^+$, found 298.10379.

$^1$H NMR (CDCl$_3$) δ: 6.69 (m, 1H), 4.53 (s, 2H), 4.28 (m, 2H), 3.88 (m, 2H), 3.72 (s, 3H), 2.26 (d, 3H, J=1.0 Hz), 1.70 (m, 6H).

Example 4

Preparation of 1,4-dimethyl-6-oxo-1,6-dihydro-pyridazin-3-ylmethyl morpholin-4-ylcarbodithioate ($Id_5$)

According to the procedure described for obtaining the compound $Id_2$, a solution of morpholine (8 µL, 0.091 mmol), $CS_2$ (10 µL, 0.165 mmol) and $K_3PO_4$ (19 mg, 0.091 mmol) in DMF (1 mL) was treated with a solution of the compound $IVd_1$ (10 mg, 0.046 mmol) in DMF (1 mL). The residue obtained was purified by column chromatography on silica gel (eluent: hexane/ethyl acetate 3:1, 1:2, and 1:4), obtaining the compound $Id_5$ (13 mg, 94%). EMAR (ESI): m/z calculated for $C_{12}H_{18}N_3O_2S_2$, 300.08349 [M+H]$^+$, found 300.08357.

$^1$H NMR (CDCl$_3$) δ: 6.70 (m, 1H), 4.54 (s, 2H), 4.33 (m, 2H), 3.96 (m, 2H), 3.77 (m, 4H), 3.72 (s, 3H), 2.27 (d, 3H, J=1.0 Hz).

Example 5

Preparation of 1,4-dimethyl-6-oxo-1,6-dihydro-pyridazin-3-ylmethyl 4-benzoylpiperazin-1-ylcarbodithioate ($Id_{11}$)

According to the procedure described for obtaining the compound $Id_2$, a solution of 1-benzoylpiperazine (13 mg, 0.068 mmol), $CS_2$ (8 µL, 0.132 mmol) and $K_3PO_4$ (14 mg, 0.068 mmol) in DMF (1 mL) was treated with a solution of the compound $IVd_I$ (10 mg, 0.046 mmol) in DMF (1 mL). The residue obtained was purified by column chromatography on silica gel (eluent: hexane/ethyl acetate 1:1, 1:2 and 1:4), obtaining the compound $Id_{11}$ (18 mg, 97%). EMAR (ESI): m/z calculated for $C_{19}H_{23}N_4O_2S_2$, 403.12569 [M+H]$^+$, found 403.12569.

$^1$H NMR (CDCl$_3$) δ: 7.43 (m, 5H), 6.71 (s, 1H), 4.53 (s, 2H), 4.18 (m, 4H), 3.84 (m, 2H), 3.72 (s, 3H), 3.65 (m, 2H), 2.26 (s, 3H).

Example 6

Preparation of 2-(1-methyl-6-oxo-1,6-dihydro-pyridazin-3-yl)ethyl Piperidin-1-ylcarbodithioate ($Ia_{15}$)

According to the procedure described for $IVd_I$, a solution of 6-(2-hydroxyethyl)-2-methyl-3(2H)-pyridazinone $VIa_{II}$ (6 mg, 0.039 mmol) in CH$_2$Cl$_2$ (6 mL) was treated with CBr$_4$ (26 mg, 0.078 mmol) and PPh$_3$ (20 mg 0.078 mmol). The residue obtained was purified by column chromatography on silica gel using methylene chloride/methanol as eluent (88:2), obtaining 6-(2-bromoethyl)-2-methyl-3(2H)-pyridazinone $IVa_{II}$ (7 mg, 83%).

$^1$H NMR (CDCl$_3$) (δ: 7.14 (d, 1H, J=9.4 Hz), 6.90 (d, 1H, J=9.4 Hz), 3.76 (s, 3H), 3.64 (t, 2H, J=7.0 Hz), 3.14 (t, 2H, J=7.0 Hz).

According to the procedure described for obtaining the compound $Id_2$, a solution of piperidine (8 µL, 0.081 mmol), $CS_2$ (9 µL, 0.147 mmol) and $K_3PO_4$ (17 mg, 0.081 mmol) in DMF (1 mL) was treated with a solution of the compound $IVa_{II}$ (10 mg, 0.046 mmol) in DMF (1 mL). The residue obtained was purified by column chromatography on silica gel (eluent: hexane/ethyl acetate 3:1, 1:1 and 1:3), obtaining the compound $Ia_{15}$ (8.5 mg, 89%). EMAR (ESI): m/z calculated for $C_{13}H_{20}N_3OS_2$, 298.10423 [M+H]$^+$, found 298.10432.

$^1$H NMR (CDCl$_3$) δ: 7.25 (d, 1H, J=9.5 Hz), 6.89 (d, 1H, J=9.5 Hz), 4.29 (m, 2H), 3.86 (m, 2H), 3.75 (s, 3H), 3.59 (t, 2H, J=7.4 Hz), 3.00 (t, 2H, J=7.4 Hz), 1.70 (m, 6H).

Example 7

Preparation of 2-(1-methyl-6-oxo-1,6-dihydro-pyridazin-3-yl)propyl Pyrrolidin-1-ylcarbodithioate ($Ia_{25}$)

According to the procedure described for $IVd_I$, a solution of 6-(2-hydroxypropyl)-2-methyl-3(2H)-pyridazinone $VIa_{II}$ (6 mg, 0.036 mmol) in CH$_2$Cl$_2$ (6 mL) was treated with CBr$_4$ (30 mg, 0.096 mmol) and PPh$_3$ (30 mg 0.114 mmol). The residue obtained was purified by column chromatography on silica gel using methylene chloride/methanol as eluent (88:2), obtaining 6-(2-bromopropyl)-2-methyl-3(2H)-pyridazinone $IVa_{II}$ (7 mg, 84%). EMAR (EI): m/z calculated for $C_8H_{11}BrN_2O$, 230.0055 [M]$^+$; found 230.0057.

$^1$H NMR (CDCl$_3$) δ: 7.11 (d, 1H, J=9.6 Hz), 6.89 (d, 1H, J=9.6 Hz), 3.75 (s, 3H), 3.47 (t, 2H, J=6.4 Hz), 2.76 (t, 2H, J=7.4 Hz), 2.22 (m, 2H).

According to the procedure described for obtaining the compound $Id_2$, a solution of pyrrolidine (8 µL, 0.096 mmol), $CS_2$ (9 µL, 0.147 mmol) and $K_3PO_4$ (17 mg, 0.081 mmol) in DMF (1 mL) was treated with a solution of the compound $IVa_{II}$ (9 mg, 0.039 mmol) in DMF (1 mL). The residue obtained was purified by column chromatography on silica gel (eluent: hexane/ethyl acetate 1:1, 1:2), obtaining the compound Ia$_{25}$ (11 mg, 95%). EMAR (ESI): m/z calculated for C$_{13}$H$_{20}$N$_3$OS$_2$, 298.10478 [M+H]$^+$, found 298.10432.

$^1$H NMR (CDCl$_3$) δ: 7.13 (d, 1H, J=9.5 Hz), 6.89 (d, 1H, J=9.5 Hz), 3.93 (t, 2H, J=6.9 Hz), 3.75 (s, 3H), 3.64 (t, 2H, J=6.8 Hz), 3.36 (t, 2H, J=7.3 Hz), 2.71 (t, 2H, J=7.6 Hz), 2.07 (m, 4H), 1.98 (m, 2H).

Example 8

Preparation of 1-benzyl-6-oxo-1,6-dihydropyridazin-4-ylmethyl N,N-diethyldithiocarbamate (IIc$_2$)

A solution of 3-(tert-butyldiphenylsyliloxymethyl)furan (3.00 g, 8.92 mmol) in dry MeOH (40 mL) was added diisopropylethylamine (7 mL, 40.20 mmol) and rose Bengal (15 mg) and was purged at RT with O$_2$ for 1 h. The reaction mixture was cooled at −78° C. and irradiated with a 200 W lamp under an O$_2$ atmosphere for 5 h. Then it was left to reach RT and the solvent was removed under vacuum. The residue obtained was dissolved in CH$_2$Cl$_2$ (40 mL) and a 0.12 M oxalic acid solution (350 mL) was added, stirring for 30 min. The resulting mixture was extracted with CH$_2$Cl$_2$ (3×100 mL) and the combined organic phases were dried, filtered and concentrated under vacuum. The residue obtained was purified by column chromatography on silica gel (eluent: ethyl acetate/hexane 1:2), with a mixture of 4-(tert-butyldiphenylsyliloxymethyl)-5-hydroxy-5H-furan-2-one XI$_1$ and of 3-(tert-butyldiphenylsyliloxymethyl)-5-hydroxy-5H-furan-2-one XV$_1$ (3.29 g, 100%) being isolated at a ratio 4:1. EMAR (ESI): m/z calculated for C$_{21}$H$_{25}$O$_4$Si, 369.15166 [M+1]; found 369.15162.

A solution of the mixture of compounds XI$_1$ y XV$_1$ (531 mg, 1.44 mmol, 4:1 ratio) in absolute ethanol (15 mL), was added benzylhydrazine dihydrochloride (BnNHNH$_2$.2HCl, 562 mg, 2.88 mmol) and Et$_3$N (0.6 mL, 4.30 mmol). The reaction mixture was stirred at reflux for 7 h. Then, the solvent was removed under vacuum, and the residue obtained was purified by column chromatography on silica gel (eluent: hexane/ethyl acetate 9:1), isolating 2-benzyl-4-(tert-butyldiphenylsyliloxymethyl)pyridazin-3(2H)-one XVIc$_1$ (43 mg, 32%) and then 2-benzyl-5-(tert-butyldiphenylsyliloxymethyl)pyridazin-3(2H)-one XIIc$_1$ (277 mg, 53%).

2-Benzyl-4-(tert-butyldiphenylsyliloxymethyl)pyridazin-3(2H)-one XVIc$_1$ EMAR (ESI): m/z calculated for C$_{28}$H$_{31}$N$_2$O$_2$Si, 455.21493 [M+1]; found 455.21371.

$^1$H-NMR (CDCl$_3$, δ): 7.85 (d, 1H, J=4.0 Hz), 7.63 (m, 4H), 7.51 (m, 1H), 7.36 (m, 11H), 5.29 (s, 2H), 4.73 (d, 2H, J=1.5 Hz), 1.12 (s, 9H).

2-Benzyl-5-(tert-butyldiphenylsyliloxymethyl)pyridazin-3(2H)-one XIIc$_1$ EMAR (ESI): m/z calculated for C$_{28}$H$_{31}$N$_2$O$_2$Si, 455.21493 [M+1]; found 455.21473.

$^1$H-NMR (CDCl$_3$, δ): 7.64 (m, 5H, H6), 7.37 (m, 11H), 6.96 (m, 1H), 5.32 (s, 2H), 4.55 (d, 2H, J=1.5 Hz), 1.09 (s, 9H).

According to the procedure described for VId, a 2-benzyl-5-(tert-butyldiphenylsyliloxymethyl)pyridazin-3(2H)-one XIIc$_1$ solution (247 mg, 0.54 mmol) in THF (5 mL), was treated with a 1M TBAF solution in THF (0.8 mL, 0.81 mmol). The residue obtained was purified by column chromatography on silica gel (eluent: ethyl acetate/methanol 98:2), obtaining 2-benzyl-5-hydroxymethylpyridazin-3(2H)-one Xc$_f$ (102 mg, 87%). EMAR (ESI): m/z calculated for C$_{12}$H$_{13}$N$_2$O$_2$, 217.09715 [M+1]; found 217.09782.

According to the procedure described for IVd$_f$, a 2-benzyl-5-hydroxymethylpyridazin-3(2H)-one Xc$_f$ solution (83 mg, 0.39 mmol) in CH$_2$Cl$_2$ (5 mL), was treated with CBr$_4$ (256 mg, 0.77 mmol) and PPh$_3$ (202 mg, 0.77 mmol). The residue was purified by column chromatography on silica gel (eluent: dichloromethane/methanol 99.5:0.5), obtaining 2-benzyl-5-bromomethylpyridazin-3(2H)-one IXc$_f$ (62 mg, 58%). EMAR (ESI): m/z calculated for C$_{12}$H$_{12}$BrN$_2$O, 279.01275 [M+1]; found 279.01210.

$^1$H-NMR (CDCl$_3$, δ): 7.77 (d, 1H, J=1.9 Hz), 7.40 (m, 2H), 7.29 (m, 3H), 6.85 (d, 1H, J=1.9 Hz), 5.30 (s, 2H), 4.17 (s, 2H).

According to the procedure described for obtaining the compound Id$_2$, a diethylamine solution (3.9 µL, 0.037 mmol), CS$_2$ (4.1 µL, 0.068 mmol) and K$_3$PO$_4$ (8 mg, 0.037 mmol) in DMF (2 mL) was treated with a solution of the compound IXc$_f$ (9.5 mg, 0.034 mmol) in DMF (2 mL). The residue obtained was purified by column chromatography on silica gel (eluent: hexane/ethyl acetate 4:1, 3:1, 2:1), obtaining the compound IIc$_2$ (10.2 mg, 86%). EMAR (ESI): m/z [M+H]$^+$ calculated for C$_{17}$H$_{22}$N$_3$OS$_2$, 348.12043, found 348.11976.

$^1$H NMR (CDCl$_3$) δ:7.84 (m, 1H), 7.43 (m, 2H), 7.32 (m, 3H), 6.91 (m, 1H), 5.30 (s, 2H), 4.45 (s, 2H), 4.03 (c, 2H, J=6.5 Hz), 3.76 (c, 2H, J=6.5 Hz), 1.30 (m, 6H).

Example 9

Preparation of 1-benzyl-6-oxo-1,6-dihydropyridazin-4-ylmethyl Pyrrolidin-1-ylcarbodithioate (IIc$_3$)

According to the procedure described for obtaining the compound Id$_2$, a pyrrolidine solution (3.2 µL, 0.038 mmol), CS$_2$ (4.1 µL, 0.068 mmol) and K$_3$PO$_4$ (8 mg, 0.037 mmol) in DMF (2 mL) was treated with a solution of the compound IXc$_f$ (10 mg, 0.035 mmol) in DMF (2 mL). The residue obtained was purified by column chromatography on silica gel (eluent: hexane/ethyl acetate 3:1, 2:1), obtaining the compound IIc$_3$ (11.7 mg, 97%). EMAR (ESI): m/z calculated for C$_{17}$H$_{20}$N$_3$OS$_2$, 348.10478 [M+H]$^+$; found 346.19423.

$^1$H NMR (CDCl$_3$) δ: 7.83 (d, 1H, J=2.1 Hz), 7.40 (m, 2H), 7.29 (m, 3H), 6.89 (m, 1H), 5.28 (s, 2H), 4.43 (s, 2H), 3.91 (t, 2H, J=6.9 HZ), 3.65 (t, 2H, J=6.9 Hz), 2.09 (q, 2H, J=6.9 Hz), 2.00 (q, 2H, J=6.9 Hz).

Example 10

Preparation of 1-benzyl-6-oxo-1,6-dihydropyridazin-4-ylmethyl Piperidin-1-ylcarbodithioate (IIc$_4$)

According to the procedure described for obtaining the compound Id$_2$, a piperidine solution (3.1 µL, 0.031 mmol), CS$_2$ (3.5 µL, 0.057 mmol) and K$_3$PO$_4$ (8 mg, 0.037 mmol) in DMF (2 mL) was treated with a solution of the compound IXc$_f$ (10 mg, 0.035 mmol) in DMF (2 mL). The residue obtained was purified by column chromatography on silica gel (eluent: hexane/ethyl acetate 4:1, 3:1, 2:1), obtaining the compound IIc$_4$ (9.4 mg, 90%). EMAR (ESI): m/z calculated for C$_{18}$H$_{22}$N$_3$OS$_2$, 360.12043 [M+H]$^+$; found 360.11968.

$^1$H NMR (CDCl$_3$) δ: 7.82 (d, 1H, J=2.3 Hz), 7.41 (m, 2H), 7.29 (m, 3H), 6.88 (m, 1H), 5.28 (s, 2H), 4.44 (s, 2H), 4.26 (m, 2H), 3.87 (m, 2H), 1.71 (m, 6H).

Example 11

Preparation of 1-benzyl-6-oxo-1,6-dihydro-pyridazin-4-ylmethyl Morpholin-4-ylcarbodithioate (IIc$_5$)

According to the procedure described for obtaining the compound Id$_2$, a morpholine solution (3.4 μL, 0.039 mmol), CS$_2$ (4.4 μL, 0.072 mmol) and K$_3$PO$_4$ (8 mg, 0.037 mmol) in DMF (2 mL) was treated with a solution of the compound IXc$_I$ (10 mg, 0.035 mmol) in DMF (2 mL). The residue obtained was purified by column chromatography on silica gel (eluent: hexane/ethyl acetate 4:1, 3:1, 2:1), obtaining the compound IIc$_5$ (12 mg, 92%). EMAR (ESI): m/z calculated for C$_{17}$H$_{20}$N$_3$O$_2$S$_2$, 362.09969 [M+H]$^+$; found 362.09914.

$^1$H NMR (CDCl$_3$) δ:7.80 (d, 1H, J=2 Hz), 7.41 (m, 2H), 7.30 (m, 3H), 6.89 (m, 1H), 5.28 (s, 2H), 4.45 (s, 2H), 4.30 (m, 2H), 3.93 (m, 2H), 3.77 (m, 4H).

Example 12

Preparation of 1-benzyl-6-oxo-1,6-dihydro-pyridazin-4-ylmethyl 4-benzoylpiperazin-1-ylcarbodithioate (IIc$_{11}$)

According to the procedure described for obtaining the compound Id$_2$, a benzoylpiperazine solution (7 mg, 0.038 mmol), CS$_2$ (4.1 μL, 0.068 mmol) and K$_3$PO$_4$ (8 mg, 0.037 mmol) in DMF (2 mL) was treated with a solution of the compound IXc$_I$ (10 mg, 0.035 mmol) in DMF (2 mL). The residue obtained was purified by column chromatography on silica gel (eluent: hexane/ethyl acetate 2:1, 1:1), obtaining the compound IIc$_{11}$ (12 mg, 74%). EMAR (ESI): m/z calculated for C$_{24}$H$_{25}$N$_4$O$_2$S$_2$, 465.14189 [M+H]$^+$; found 465.14134.

$^1$H NMR (CDCl$_3$) δ: 7.89 (d, 1H, J=2.3 Hz), 7.43 (m, 7H), 7.30 (m, 3H), 6.89 (m, 1H), 5.28 (s, 2H), 4.44 (s, 2H), 4.39-3.54 (m, 8H).

Example 13

Preparation of 1-benzyl-6-oxo-1,6-dihydro-pyridazin-5-ylmethyl Pyrrolidin-1-ylcarbodithioate (IIIc$_3$)

According to the procedure described for VId$_I$, a 2-benzyl-4-(tert-butyldiphenylsyliloxymethyl)pyridazin-3(2H)-one XVIc$_I$ solution (70 mg, 0.15 mmol) in THF (5 mL) was treated with a 1M TBAF solution in THF (0.2 mL, 0.23 mmol). The residue obtained was purified by column chromatography on silica gel (eluent: ethyl acetate/methanol 98:2), obtaining 2-benzyl-4-hydroxymethylpyridazin-3(2H)-one XIVc$_I$ (25 mg, 75%). EMAR (ESI): m/z calculated for C$_{12}$H$_{13}$N$_2$O$_2$, 217.09715 [M+1]; found 217.09651.

According to the procedure described for IVd$_I$, a 2-benzyl-4-hydroxymethylpyridazin-3(2H)-one XIVc$_I$ solution (29 mg, 0.13 mmol) in CH$_2$Cl$_2$ (5 mL) was treated with CBr$_4$ (90 mg, 0.27 mmol) and PPh$_3$ (70 mg, 0.27 mmol). The residue was purified by column chromatography on silica gel (eluent: hexane/ethyl acetate 6:1) obtaining 2-benzyl-4-bromomethylpyridazin-3(2H)-one XIIIc$_I$ (31 mg, 84%).

$^1$H NMR (CDCl$_3$) δ: 7.77 (d, 1H, J=4 Hz), 7.46-7.41 (m, 2H), 7.36-7.27 (m, 4H), 5.35 (s, 2H), 4.39 (s, 2H).

According to the procedure described for obtaining the compound Id$_2$, a pyrrolidine solution (3.9 μL, 0.046 mmol), CS$_2$ (4.4 μL, 0.072 mmol) and K$_3$PO$_4$ (8 mg, 0.037 mmol) in DMF (2 mL) was treated with a solution of the compound XIIIc$_I$ (10 mg, 0.035 mmol) in DMF (2 mL). The residue obtained was purified by column chromatography on silica gel (eluent: dichloromethane/methanol 98:2), obtaining the compound IIIc$_3$ (6.6 mg, 55%). EMAR (ESI): m/z calculated for C$_{17}$H$_{20}$N$_3$OS$_2$, 346.10478 [M+H]$^+$; found 346.10451.

$^1$H NMR (CDCl$_3$) δ: 7.70 (d, 1H, J=4.1 Hz), 7.51 (d, 1H, J=4.1 Hz) 7.41-4.43 (m, 2H), 7.33-7.26 (m, 3H), 5.32 (s, 2H), 4.54 (s, 2H), 3.90 (t, 2H, J=6.7 HZ), 3.63 (t, 2H, J=6.7 Hz), 2.05 (q, 2H, J=6.7 Hz), 1.95 (q, 2H, J=6.7 Hz).

Example 14

Preparation of 1-benzyl-6-oxo-1,6-dihydro-pyridazin-5-ylmethyl Morpholin-4-ylcarbodithioate (IIIc$_5$)

According to the procedure described for obtaining the compound Id$_2$, a morpholine solution (7 μL, 0.080 mmol), CS$_2$ (10 μL, 0.160 mmol) and K$_3$PO$_4$ (17 mg, 0.079 mmol) in DMF (2 mL) was treated with a solution of the compound XIIIc$_I$ (11 mg, 0.040 mmol) in DMF (2 mL). The residue obtained was purified by column chromatography on silica gel (eluent: hexane/ethyl acetate 3:1), obtaining the compound IIIc$_5$ (14 mg, 97%).

EMAR (ESI): m/z calculated for C$_{17}$H$_{20}$N$_3$O$_2$S$_2$, 362.09969 [M+H]$^+$; found 362.09914.

$^1$H NMR (CDCl$_3$) δ: 7.71 (d, 1H, J=4.1 Hz), 7.47 (d, 1H, J=4.1 Hz), 7.42 (d, 2H, J=6.8 Hz), 7.34-7.26 (m, 3H), 5.31 (s, 2H), 4.55 (s, 2H), 4.38-4.23 (m, 2H), 4.11-3.98 (m, 2H), 3.81-3.73 (m, 4H).

Example 15

Preparation of 1-benzyl-6-oxo-1,6-dihydro-pyridazin-4-ylmethyl 4-benzoylpiperazin-1-ylcarbodithioate (IIIc$_{11}$)

According to the procedure described for obtaining the compound Id$_2$, a solution of benzoylpiperazine (11.4 mg, 0.060 mmol), CS$_2$ (7 μL, 0.112 mmol) and K$_3$PO$_4$ (13 mg, 0,060 mmol) in DMF (2 mL), was treated with a solution of the compound XIIIc$_I$ (9 mg, 0.030 mmol) in DMF (2 mL). The residue obtained was purified by column chromatography on silica gel (eluent: dichloromethane, dichloromethane/methanol 99:1), obtaining the compound IIIc$_{11}$ (14 mg, 100%).

EMAR (ESI): m/z calculated for C$_{24}$H$_{25}$N$_4$O$_2$S$_2$, 465.14189 [M+H]$^+$; found 465.14071.

$^1$H NMR (CDCl$_3$) δ: 7.73 (d, 1H, J=4.0 Hz), 7.48 (d, 1H, J=4.0 Hz), 7.42 (m, 7H), 7.31 (m, 3H), 5.33 (s, 2H), 4.56 (s, 2H), 4.18 (m, 4H), 3.83 (m, 2H), 3.62 (m, 2H).

Inhibition of MAOs
Determination of MAO Isoforms Activity

The effects of compounds of formulas I, II and III on monoamine oxidase were determined by measuring the production of hydrogen peroxide (H$_2$O$_2$), and therefore the production of resorufin from p-tyramine, a substrate common to both isoenzymes (MAO-A and MAO-B). This was performed by using Amplex® Red reagent (Molecular Probes, Eugene, Oreg., USA) and MAO isoforms present in the microsomal fraction, prepared from insect cells (BTI-TN-5B1-4) infected with recombinant baculovirus, containing human MAO-A or MAO-B cDNA (Sigma-Aldrich Química S.A., Alcobendas, Spain).

Production of H$_2$O$_2$ catalysed by the 2 MAO isoforms can be detected by using Amplex® Red reagent (10-acetyl-3,7- dihydroxyphenoxazine), a non-fluorescent substance, highly sensitive, which reacts with $H_2O_2$ in the presence of horseradish peroxidase for producing a fluorescent product, resorufin.

In our experiments, the MAO activity was assessed with the above mentioned method, adapting the general process previously described (Biochem. Biophys. Res. Comm. 344, 688-695, 2006).

In the first place, 0.1 ml of sodium phosphate buffer (0.05 M, pH 7.4) was incubated, containing different concentrations of the novel compounds under study (or reference inhibitors) and the amount of human recombinant MAO-A or MAOB required for obtaining in our experimental conditions the same reaction speed in the presence of both isoenzymes; that is, for oxidizing, in the absence of drugs (control group), 165 pmoles of p-tyramine per minute (MAO-A: 1.1 µg; specific activity: 150 nmoles of p-tyramine oxidized to p-hydroxyphenylacetaldehyde per minute per protein mg; MAO-B: 7.5 µg; specific activity: 22 nmoles of p-tyramine transformed per minute per protein mg). Said incubation was performed for 15 minutes at 37° C. in 96 well plates with black and flat bottom (Microtest™ plate, BD, Franklin Lakes, N.J., USA), already placed in the light-tight chamber of the fluorescence reader (see the model below). After incubation period, reaction was started by adding (final concentrations) 200 µM of Amplex® Red reagent, 1 unit (U)/ml of horseradish peroxidase and 1 mM of p-tyramine as substrate, both for studies carried out with MAO-A and those carried out with MAO-B.

$H_2O_2$ and, accordingly, resorufin production was quantified at 37° C. in a plate fluorescence reader (FLX800™, Bio-Tek® Instruments, Inc., Winooski, Vt., EE.UU.), determining the fluorescence generated (excitation 545 nm, emission 590 nm) for 15 minutes, a period in which the increase of fluorescence was linear from the beginning.

Simultaneously, control experiments were conducted substituting the drugs (compounds of formulas I, II and III or reference inhibitors) with the appropriate vehicle dilutions. Furthermore, it was determined the possible capacity of the drugs for modifying the fluorescence generated in the reaction mixture by a non-enzymatic inhibition (for example, by direct reaction with the Amplex® Red reagent), and for that reason the drugs were added to solutions containing only the Amplex® Red reagent in a sodium phosphate buffer.

Specific fluorescence emission was calculated (used for obtaining the final results) after subtracting the background activity, being determined in vials in which solutions with MAO isoforms were substituted by sodium phosphate buffer.

Statistical Data and Analysis Presentation

Unless otherwise indicated, the results shown in the text and in the tables are expressed as the mean±mean standard error (m.s.e.) of five experiments. The statistically significant difference between two means ($P<0.05$ or $P<0.01$) was determined by one-way analysis of variance (ANOVA), followed by Dunnett's multiple comparison test.

In order to study the possible effects of the compounds of formulas I, II and III, and of the reference inhibitors, about the enzymatic activity of the MAO isoforms, fluorescence per time unit was assessed (quantified as random fluorescence/minute units) and indirectly $H_2O_2$ production; and accordingly, the pmoles/min of resorufin produced in the reaction between $H_2O_2$ and Amplex® Red reagent. In order to achieve that, several concentrations of resorufin were used with the purpose of creating a standard curve, being X=pmoles of resorufin and Y=fluorescence random units. The pmoles of resorufin produced are equivalent to the pmoles of oxidised p-tyramine, since stoichiometry of the reaction is 1:1.

In these experiments, MAOI activity of the compounds of formula I, II and III and that of the reference inhibitors is expressed as $IC_{50}$, that is, the required concentration of each compound for producing a reduction in the control value of the MAO isoforms enzymatic activity by 50%. For determining the $IC_{50}$ of each compound the computer program Origin™ 5.0 (Microcal Software, Inc., Northampton, Mass., USA) was used. The $IC_{50}$ values were calculated from the straight lines equations obtained by linear regression (method of the least squares) of the points resulting from representing the log of the molar concentration of the compound studied (axis of abscissas) against the percentage of the control MAO activity inhibition achieved with said concentration (axis of ordinates). This linear regression was performed using for each compound the data obtained with 4 to 6 concentrations capable of inhibiting between 20% and 80% of the control enzymatic activity of MAO isoenzymes. Furthermore, the ratio was calculated [$IC_{50}$ (MAO-A)]/[$IC_{50}$ (MAO-B)] as an indicator of selectivity in the inhibition shown on both isoforms.

Drugs and Chemical Compounds

The drugs and chemical substances used in the experiments were compounds of formulas I, II and III, moclobemide (kindly provided by Hoffman-La Roche Laboratories, Basel, Switzerland), selegiline and iproniazid phosphate (acquired in Sigma-Aldrich, Spain), resorufin sodium salt, clorgiline hydrochloride, p-tyramine hydrochloride, sodium phosphate and horseradish peroxidase (provided in the MAO assay kit Amplex® Red of Molecular Probes).

Appropriate dilutions of the above compounds were prepared in Milli-Q® water (Millipore Ibérica S.A., Madrid, Spain) every day before using thereof, from the following concentrated stock solutions kept at −20° C.: compounds of formulas I, II and III (0.1 M) in dimethyl sulphoxide (DMSO, Sigma-Aldrich); selegiline, moclobemide, iproniazid, resorufin, clorgiline, p-tyramine and horseradish peroxidase (0.1 M) in Milli-Q® water.

Due to photosensitivity of some of the substances being used (for example, Amplex® Red reagent), all experiments were performed in darkness. In any of the assays, neither Milli-Q® water nor the vehicle being used (DMSO) showed a significant pharmacological effect.

Results

The compounds used for the present invention of the general formula I, II and III are selective inhibitors of MAO-B. Table XI show the $IC_{50}$ values in micromoles/L (µM) of the compounds detailed above ($Id_2$, $Id_3$, $Id_4$, $Id_5$, $Id_{11}$, $Ia_{15}$, $Ia_{25}$, $IIc_2$, $IIc_3$, $IIc_4$, $IIc_5$, $IIc_{11}$, $IIIc_3$, $IIIc_5$, $IIIc_{11}$).

TABLE XI

IC$_{50}$ values of the studied compounds (including reference inhibitors) on enzymatic activity of human recombinant MAO isoforms and selectivity index for MAO-B ([IC$_{50}$ (MAO-A)]/[IC$_{50}$ (MAO-B)]).

| Compound | IC$_{50}$ hMAO-A (μM) | IC$_{50}$ hMAO-B (μM) | S.I. |
|---|---|---|---|
| Id$_2$ | *** | *** | — |
| Id$_3$ | ** | * | — |
| Id$_4$ | *** | 7.48 ± 0.34 | 13.4 |
| Id$_5$ | *** | 38.57 ± 1.74 | 2.6 |
| Id$_{11}$ | *** | 44.53 ± 2.00 | 2.2 |
| Ia$_{15}$ | ** | 11.88 ± 0.53 | >8.4[b] |
| Ia$_{25}$ | ** | 66.49 ± 4.43 | >1.5[b] |
| IIc$_2$ | ** | 44.25 ± 2.95 | >2.3[b] |
| IIc$_3$ | *** | 9.68 ± 0.65 | 10.3 |
| IIc$_4$ | ** | 6.71 ± 0.45 | >15[b] |
| IIc$_5$ | ** | *** | — |
| IIc$_{11}$ | ** | ** | — |
| IIIc$_3$ | ** | 33.96 ± 2.26 | >2.9[b] |
| IIIc$_5$ | ** | 24.05 ± 1.60 | >4.2[b] |
| IIIc$_{11}$ | ** | ** | — |
| Clorgiline | 0.0052 ± 0.00092[a] | 63.41 ± 1.20 | 0.000082 |
| Selegiline | 68.73 ± 4.21[a] | 0.017 ± 0.0019 | 4.043 |
| Iproniazid | 6.56 ± 0.76 | 7.54 ± 0.36 | 0.87 |
| Moclobemide | 361.38 ± 19.37 | * | <0.36[b] |

Each IC$_{50}$ value is the mean ± mean standard deviation of 5 experiments (n = 5).
[a]P < 0.01 with respect to the corresponding IC$_{50}$ value obtained against MAO-B, determined by ANOVA/Dunnett's test.
[b]Value calculated considering as IC50 against MAO-A or MAO-B the highest concentration studied (100 μM or 1 mM).
* Inactive at 1 mM (highest concentration studied)
** Inactive at 100 μM (highest concentration assayed). At higher concentrations the compound precipitates.
*** At 100 μM inhibit enzymatic activity by 45-50%. At higher concentrations the compound precipitates.
SI: Selectivity index hMAO-B = IC$_{50}$ (hMAO-A)/IC$_{50}$ (hMAO-B)

Most of the compounds of the general formula I, II and III detailed in the table are inactive against MAO-A and inhibit MAO-B with IC$_{50}$ values in the micromolar range.

IC$_{50}$ values of the compounds of the general formula I, II and III against MAO-B are comparable to those exhibited by some of the reference inhibitors used in the study, such as for example iproniazid (MAO-A/MAO-B dual inhibitor), but having higher MAO-B selectivity indexes.

The results obtained indicate that MAO-B activity and selectivity of the compounds of general formula I, II and III is more influenced by the type of amine present in the dithiocarbamate moiety than by the position and magnitude of the alkyl chain, and by the nature of the substituent in N of the pyridazinone ring.

Therefore, incorporating dithiocarbamate moieties to the pyridazinone ring into position 4, 5 or 6 through an alkyl chain of variable length, which results in the compounds of general formula I, II and III, provides selective MAO-B inhibitors the structure of which is highly novel for this type of activity, since no pyridazinone derivatives are known which act as selective inhibitors of MAO isoform B.

The invention claimed is:

1. A compound of formula (I), (II) or (III):

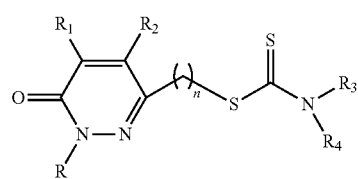

I

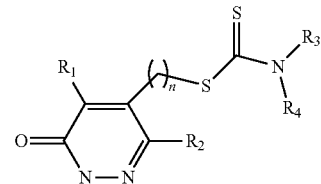

II

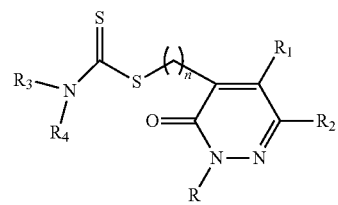

III wherein,
n is an integer number selected from 1, 2, 3, 4, 5, 6, 7, 8;
R is selected from H, —C$_1$-C$_6$ alkyl, —C$_1$-C$_6$ carboxyalkyl, —C$_1$-C$_6$ haloalkyl, —C$_6$-C$_{12}$ aryl, —C$_6$-C$_{12}$ aralkyl or —C$_4$-C$_{12}$ heteroaryl;
R$^1$ is selected from H, —C$_1$-C$_6$ alkyl or an halogen;
R$^2$ is selected from H, —C$_1$-C$_6$ alkyl or an halogen;
R$^3$, R$^4$ are independently selected from H, —C$_1$-C$_6$ alkyl, saturated —C$_1$-C$_6$ heterocycloalkyl, —C$_6$-C$_{12}$ aryl, —C$_6$-C$_{12}$ aralkyl or —C$_4$-C$_{12}$ heteroaryl; or R$^3$ and R$^4$ form a cycle selected from C$_5$-C$_8$ cycloalkyl, C$_5$-C$_8$ heterocycloalkyl, N-alkyl substituted C$_5$-C$_8$ heterocycloalkyl, N-aryl substituted C$_5$-C$_8$ heterocycloalkyl, N-cycloalkyl substituted C$_5$-C$_8$ heterocycloalkyl, N-aralkyl substituted C$_5$-C$_8$ heterocycloalkyl or N-acyl substituted C$_5$-C$_8$ heterocycloalkyl;
and pharmaceutically acceptable salts thereof.

2. The compound according to claim 1, wherein n is an integer number selected from 1, 2, or 3.

3. The compound according to claim 1, wherein R is a group selected from methyl, phenyl or benzyl.

4. The compound according to claim 1, wherein $R^1$ is a hydrogen atom.

5. The compound according to claim 1, where $R^2$ is a hydrogen atom or a methyl group.

6. The compound according to claim 1, wherein $R^3$ and $R^4$ form a group selected from the group consisting of:

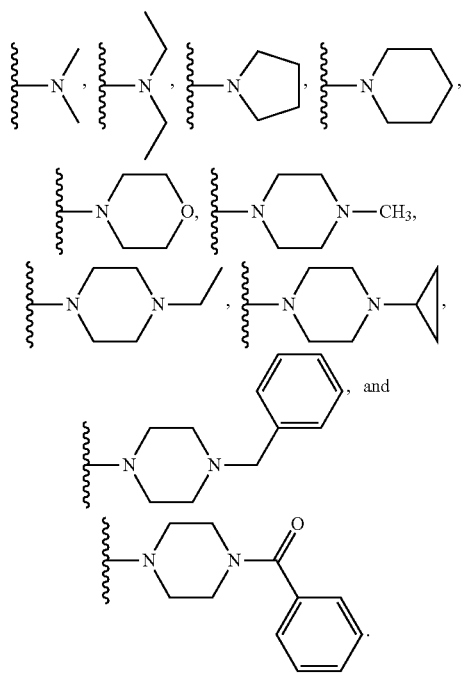

7. The compound according to claim 1, selected from the group consisting of:

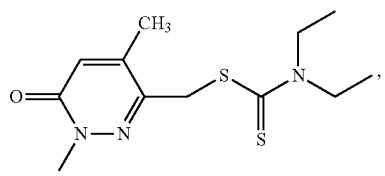
Id$_2$

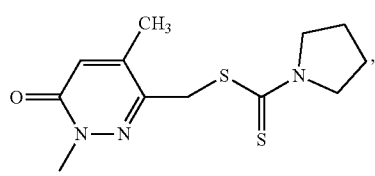
Id$_3$

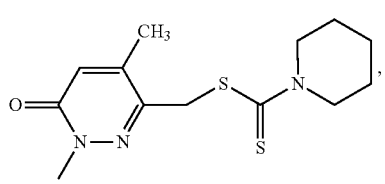
Id$_4$

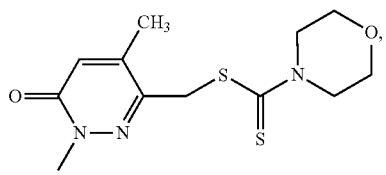
Id$_5$

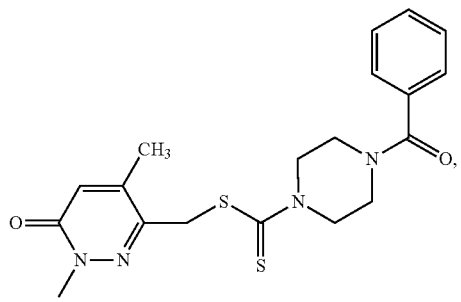
Id$_{11}$

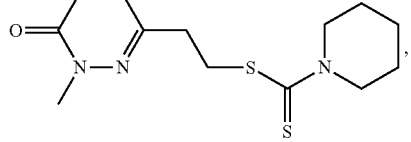
Ia$_{15}$

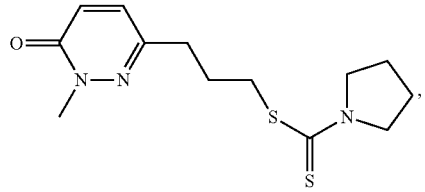
Ia$_{25}$

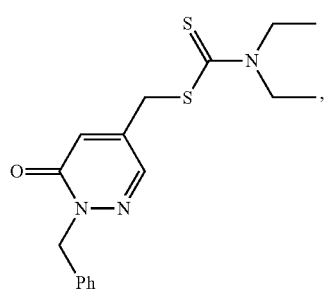
IIc$_2$

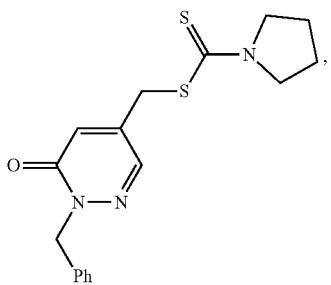
IIc$_3$

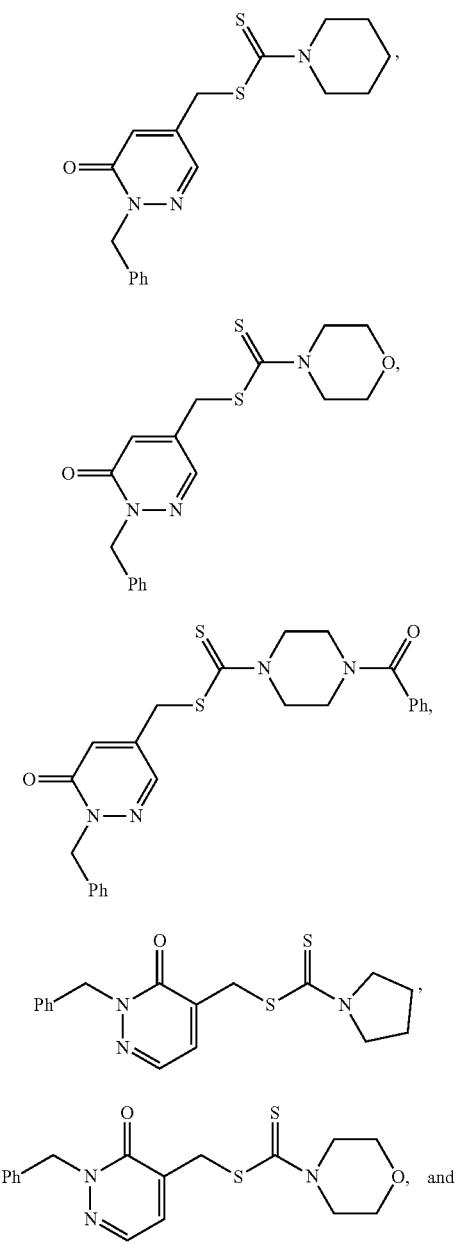

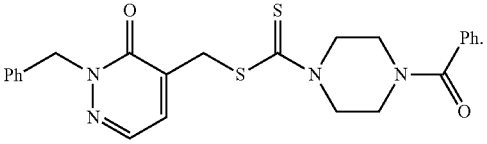

8. The pharmaceutical composition comprising a compound of formula (I), (II) or (III) according to claim 1, a pharmaceutically acceptable carrier and at least one pharmaceutically acceptable excipient.

9. The pharmaceutical composition according to claim 8, comprising at least one additional therapeutic agent.

10. A method of treating disorders derived from MAO-B hyperactivity comprising administering a compound of formula (I), (II), or (III) according to claim 1 to a mammal in need thereof, wherein the disorder is selected from Parkinson, Alzheimer, senile dementia or ataxia.

11. A method for the synthesis of a compound of formula (I), (II) or (III) according to claim 1, comprising a stage as described in scheme 1, wherein 6(5) (4)-bromoalkyl-3(2H)-pyridazinone of formula (IV), (IX) or (XIII), a secondary amine of formula V and carbon disulphide ($CS_2$) react in the presence of a base in a solvent at room temperature

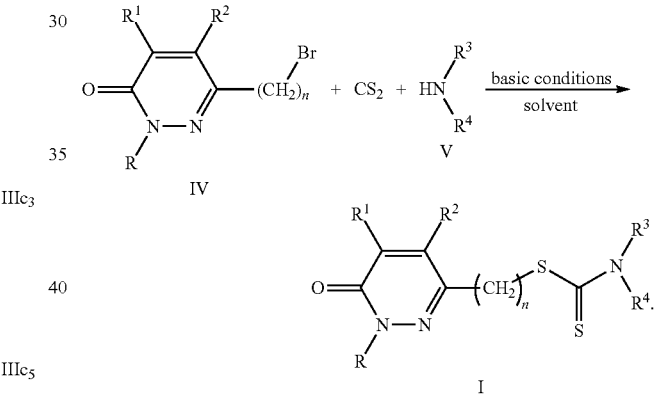

Scheme 1

12. The method according to claim 11, wherein the solvent is dimethylformamide (DMF) and the base is $K_3PO_4$.

* * * * *